(12) United States Patent
Truckai et al.

(10) Patent No.: US 7,125,409 B2
(45) Date of Patent: Oct. 24, 2006

(54) ELECTROSURGICAL WORKING END FOR CONTROLLED ENERGY DELIVERY

(75) Inventors: Csaba Truckai, Saratoga, CA (US); John Shadduck, Tiburon, CA (US)

(73) Assignee: SurgRx, Inc., Palo Alto, CA (US)

( * ) Notice: Subject to any disclaimer, the term of this patent is extended or adjusted under 35 U.S.C. 154(b) by 0 days.

(21) Appl. No.: 11/315,418

(22) Filed: Dec. 21, 2005

(65) Prior Publication Data

US 2006/0111706 A1      May 25, 2006

Related U.S. Application Data

(63) Continuation of application No. 10/643,787, filed on Aug. 19, 2003, now Pat. No. 7,070,597.

(51) Int. Cl.
    *A61B 18/12*  (2006.01)
(52) U.S. Cl. .......................... 606/49; 606/41
(58) Field of Classification Search ............... 600/373; 606/32, 38, 41, 42; 607/115
    See application file for complete search history.

(56) References Cited

U.S. PATENT DOCUMENTS

| | | | | |
|---|---|---|---|---|
| 5,593,406 A | * | 1/1997 | Eggers et al. | 606/29 |
| 5,807,392 A | * | 9/1998 | Eggers | 606/31 |
| 5,911,719 A | * | 6/1999 | Eggers | 606/31 |
| 6,106,558 A | * | 8/2000 | Picha | 623/23.74 |
| 6,107,699 A | * | 8/2000 | Swanson | 307/112 |
| 6,113,598 A | * | 9/2000 | Baker | 606/51 |
| 6,132,426 A | * | 10/2000 | Kroll | 606/41 |
| 6,143,207 A | * | 11/2000 | Yamada et al. | 252/515 |
| 6,176,857 B1 | * | 1/2001 | Ashley | 606/32 |
| 6,273,887 B1 | * | 8/2001 | Yamauchi et al. | 606/48 |

* cited by examiner

*Primary Examiner*—Roy D. Gibson
*Assistant Examiner*—Aaron Roane
(74) *Attorney, Agent, or Firm*—Townsend and Townsend and Crew LLP

(57) ABSTRACT

An electrosurgical working end for automatic modulation of active Rf density in a targeted tissue volume. The working end of the probe of the present invention defines a tissue-engagement surface of an elastomeric material with conductive elements that extend therethrough. In one embodiment, the expansion of the elastomeric material can de-couple the conductive elements from an interior electrode based temperature to modulate current flow. In another embodiment, the elastomeric material can couple and de-couple the conductive elements from an interior electrode based on engagement pressure to modulate current flow

19 Claims, 39 Drawing Sheets

ELECTROSURGICAL WORKING END FOR CONTROLLED ENERGY DELIVERY

CROSS-REFERENCES TO RELATED APPLICATIONS

This application is a continuation of U.S. patent application Ser. No. 10/643,787 filed Aug. 19, 2003 now U.S. Pat. No. 7,070,597, which claimed the benefit of priority of U.S. Provisional Patent Application Ser. No. 60/404,703 filed Aug. 19, 2002, both of which are fully incorporated herein by reference. U.S. patent application Ser. No. 10/643,787 is also a Continuation-In-Part of U.S. patent applications: Ser. No. 10/982,482 filed Oct. 18, 2001 entitled Electrosurgical Working End for Controlled Energy Delivery and Ser. No. 10/032,867 filed Oct. 22, 2001 entitled Electrosurgical Jaw Structure for Controlled Energy Delivery, now U.S. Pat. No. 6,929,644, all of which are fully incorporated herein by reference.

BACKGROUND OF THE INVENTION

1. Field of the Invention

This invention relates to systems and methods for delivering energy to tissue, and more particularly to systems for hyperthermic treatment or ablation of targeted tissues, such as tumors and the like. The system of the invention maintains a selected energy delivery profile in a targeted tissue volume to effectively localize thermal effects for a selected time interval.

2. Description of the Related Art

In recent years, a number of instruments have been disclosed for localized thermally-mediated treatments or ablations of tumors or other targeted tissues in an interior of a patient's body. Any such percutaneous or minimally invasive treatment offers the advantage of causing less damage to healthy tissue when compared to an open surgical procedure, for example an excision of a tumor. Further, a localized thermal treatment of a tumor can prevent seeding of the tumor which is believed to be a risk factor in an open surgery.

Several terms have been used to describe such thermally-mediated treatments, generally depending on the temperature range of the therapy, including terms such as hyperthermia, thermotherapy and ablation. Hyperthermia often is used to describe therapies that cause tissue temperatures in the range of 37° C. to about 45° C. or higher that do not cause immediate cell disruption and death. The term ablation typically describes temperature ranges that denature proteins, such as in coagulation, for example in the 50–100° C. range and higher. This disclosure relates to the controlled application of energy to tissue in any thermotherapy, and will typically use the terms thermally-mediated therapy or ablation to describe the methods of the invention that cover temperature ranges from about 37° C. to 200° C.

An exemplary thermally-mediated therapy of the invention is the ablation of tumors, whether benign or malignant, for example tumors of the liver. In a prior art therapy, heat has been applied to a tumor by means of direct contact of the targeted tissue with an exposed radio-frequency (Rf) electrode carried at the distal end of a insulated needle-type probe as depicted in FIG. 1A (see, e.g., U.S. Pat. No. 5,507,743). The principal problem related to the use of Rf electrode needles is that the tissue volume elevated in temperature is not adequately controlled and localized. For example, it may be desirable to maintain a targeted tissue region between 65° C. and 70° C. for 300 seconds. FIG. 1A illustrates the active heating of tissue around the needle electrode at time $T_1$ which comprises a time interval just after the initiation of mono-polar Rf flow through the tissue (ground pad not shown). The arrows in FIG. 1A depict the application of Rf energy fairly deep into the tissue volume. Next, FIG. 1B illustrates that the active heating of tissue at time $T_2$ around the electrode, which is limited in depth as indicated by the arrows. In a typical treatment with a fine needle, the initial active Rf energy will dehydrate or even desiccate tissue around the needle, and probably coagulate microvasculature. The result can be an elevation of the tissue's impedance (due to lack of fluid in the tissue) that is not altered by migration of body fluids to the site. Thus, even if Rf power delivery to the tissue is modulated by a feedback mechanism, such as impedance monitoring, the lack of the fluid content in the tissue may never allow substantial deep active Rf energy in the tissue volume around the electrode.

What is needed is a system and method for delivery of Rf energy to targeted tissue volumes in a precisely controlled manner for localization of thermal effects. It would desirable to provide an Rf system that can maintain a selected tissue temperature, and Rf density in tissue, independent of changes in voltage or current and without the need for feedback mechanisms.

BRIEF SUMMARY OF THE INVENTION

In general, the various embodiments of probes corresponding to the present invention all provide an Rf working end that is adapted to instantly and automatically modulate active Rf energy density in a targeted tissue without reliance of prior art "feedback" monitoring systems that measure impedance, temperature, voltage or a combination thereof. In an exemplary embodiment, a needle-type probe can be used for tumor ablation.

The energy delivery member of any probe of the present invention defines a tissue-engagement plane that is adapted to contact the targeted tissue. A cross-section of the working end interior of the engagement plane explains the multiple components that comprise the invention for applying energy to tissue. Typically, the engagement plane defines a thin surface conductive layer portion (for tissue contact) that overlies a medial conductive matrix of a temperature sensitive resistive material. Interior of the medial conductive matrix is an inner or core conductive material (an electrode) that is coupled to an Rf source and controller. Of particular interest, the medial conductive matrix comprises a positive temperature coefficient (PTC) having a resistance (i.e., impedance to electrical conduction therethrough) that changes as it increases in temperature. One type of PTC material is a ceramic that is engineered to exhibit a dramatically increasing resistance (i.e., several orders of magnitude) above a specific temperature of the material-a Curie point or switching range.

The working end of the invention utilizes a medial variable conductive matrix that has a selected switching range, for example a narrow 2–5° C. range, which approximates the target temperature of the thermally-mediated therapy. In operation, it can be understood that the engagement plane will apply active Rf energy to the engaged tissue until the medial conductive matrix is heated to the selected switching range. When the tissue temperature thus elevates the temperature of the medial PTC conductive layer to the switching range, Rf current flow from the core conductive electrode through to the engagement surface will be terminated due to the exponential increase in the resistance of medial conductive matrix. This instant and automatic reduction of Rf energy application can be relied on to prevent any substantial dehydration of tissue proximate to the probe's engagement plane. By thus maintaining an optimal level of moisture around the engagement plane, the working end can more effectively apply energy to the tissue—and provide a deeper thermal effect than would be possible with prior art Rf needles.

The working end of the probe corresponding to the invention further provides a suitable cross-section and mass for maintaining heat. Thus, when the medial variable conductive matrix is elevated in temperature to its switching range, the conductive matrix can effectively function as a resistive electrode to thereafter passively conduct thermal energy to the engaged tissue volume. Thus, in operation, the working end can automatically modulate the application of energy to tissue between active Rf heating and passive conductive heating of the targeted tissue to maintain the targeted temperature level.

The working end of the probe can be have the form of a needle for piercing into tissue, and applicator surface for contacting a tissue surface or at least one surface of a jaw structure for clamping against tissue. The working end of the probe further can comprise a plurality of energy delivery members, operating in a mono-polar or bi-polar mode. In a further embodiment of the invention, the Rf treatment system can carry a fluid an infusion system for introducing an electrolyte to the engagement surface.

BRIEF DESCRIPTION OF THE DRAWINGS

Other objects and advantages of the present invention will be understood by reference to the following detailed description of the invention when considered in combination with the accompanying Figures, in which like reference numerals are used to identify like elements throughout this disclosure.

DETAILED DESCRIPTION OF THE INVENTION

Figure 2:
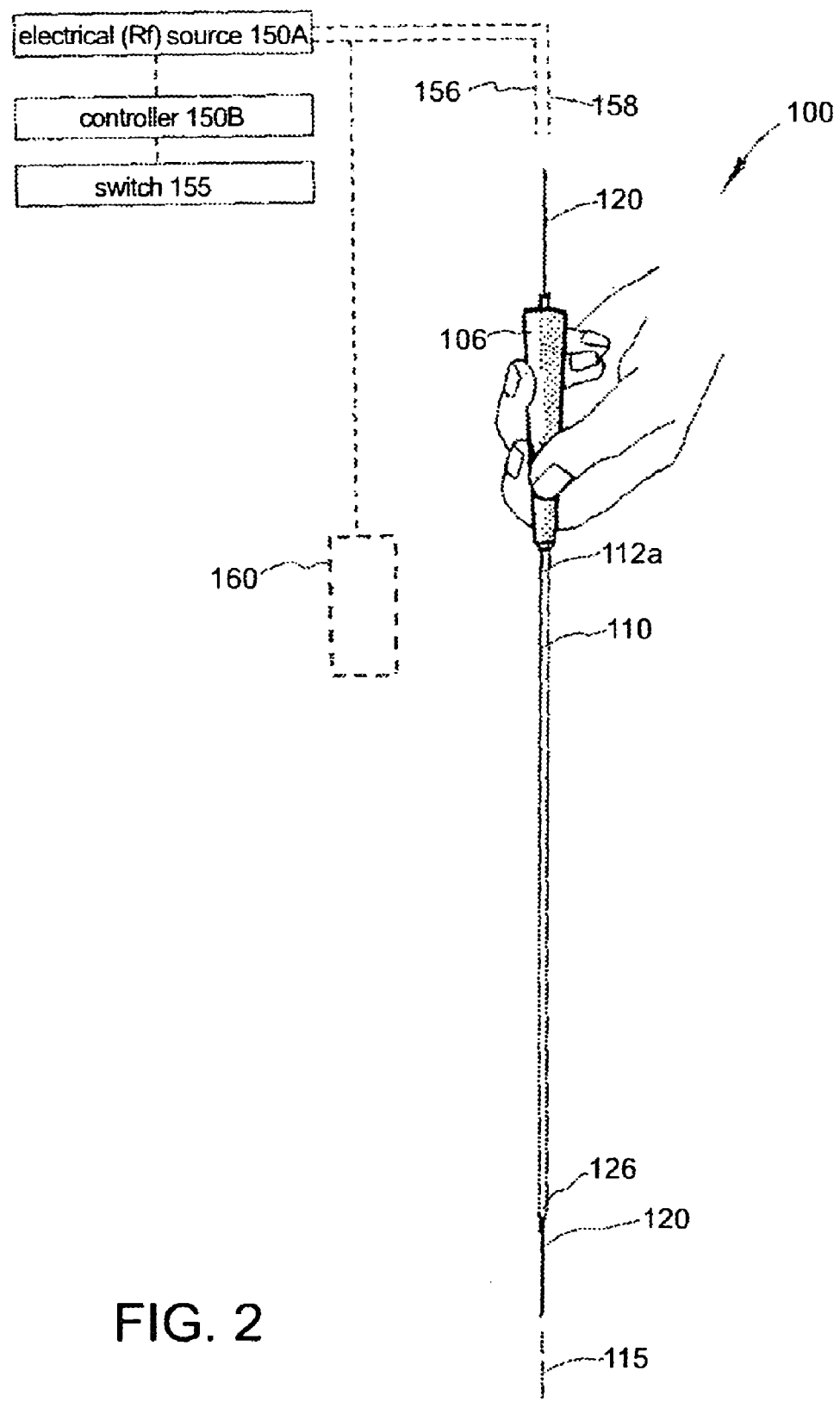
FIG. 2 is a plan view of an exemplary Type "A" probe in accordance with the invention.
Figure 3:
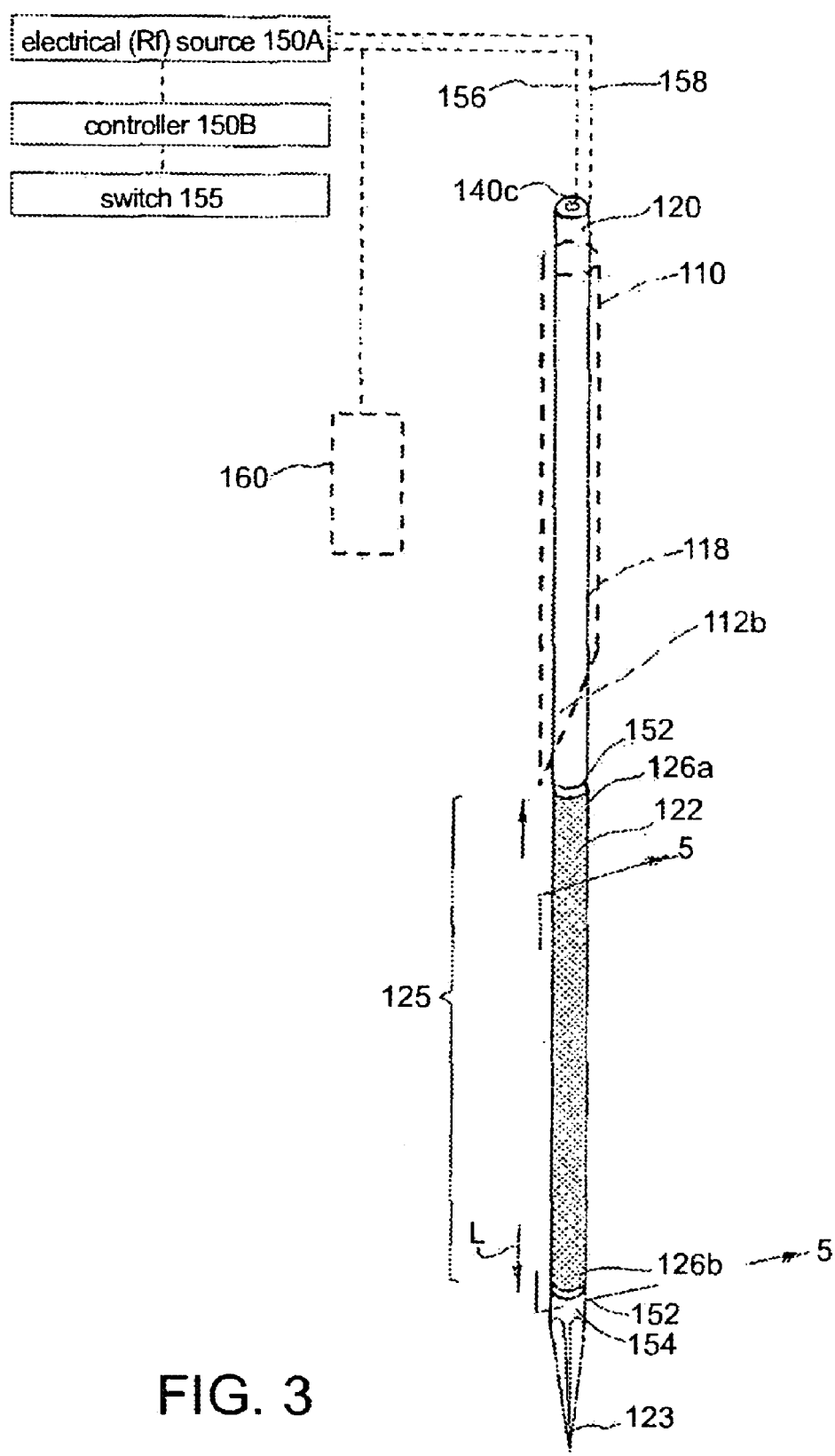
FIG. 3 is an enlarged view of the working end of the Type "A" probe of FIG. 2.
Figure 4:
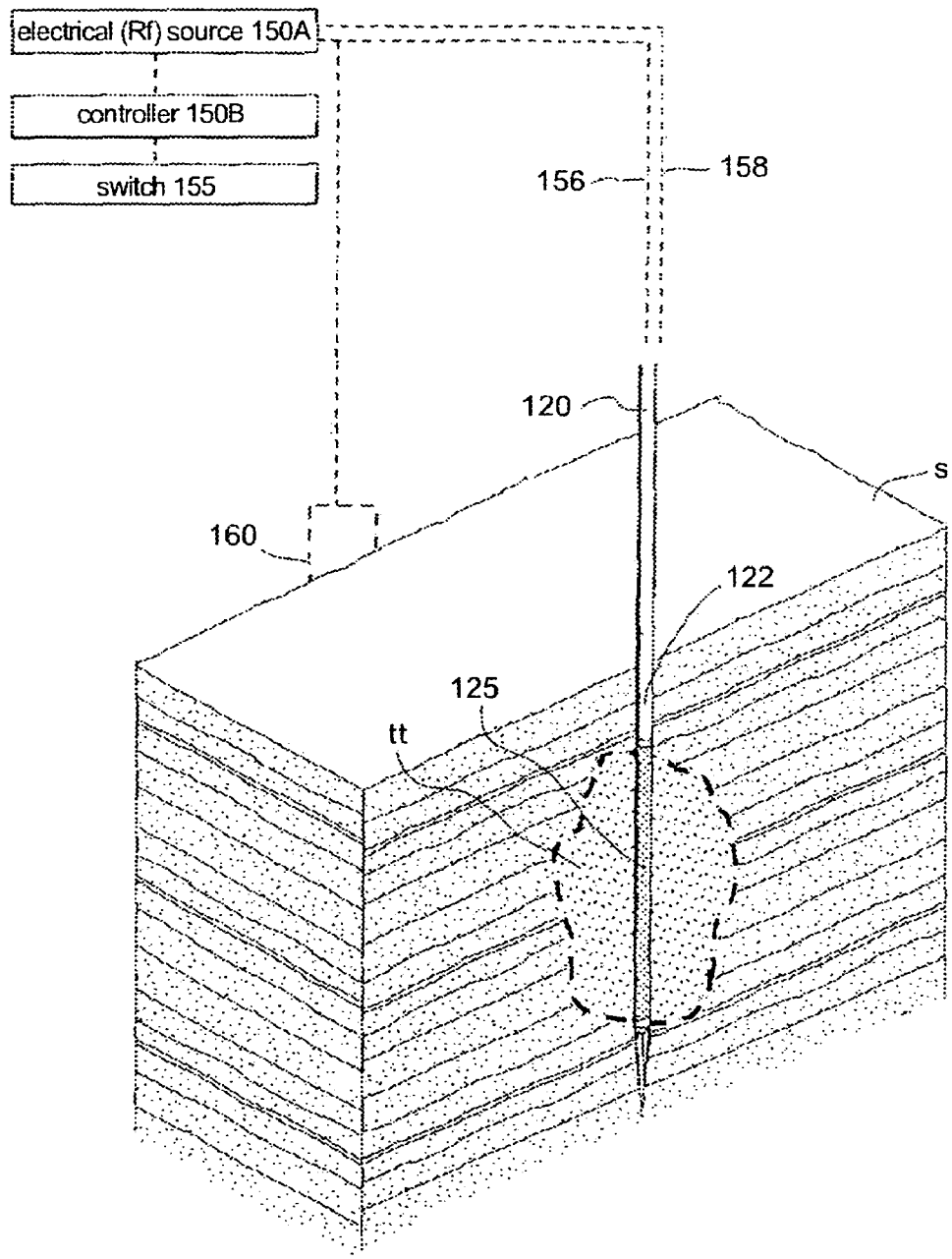
FIG. 4 is a sectional view of a tissue mass and a tumor with the working end of the probe of FIG. 2 positioned therein.

1. Type "A" probe for tumor ablation. An exemplary Type "A" probe 100 of the invention is illustrated in FIGS. 2 and 3 that is adapted for energy delivery to tissue, such as a targeted benign or malignant tumor. The probe 100 includes a proximal handle portion indicated at 106 and an introducer portion 110 that can be rigid or flexible in any suitable diameter. For example, the introducer portion 110 can be a diameter ranging from about 1 mm to 5 mm for use in percutaneous procedures or endoscopic procedures. The introducer portion extends from a proximal end 112a to a distal end 112b relative to longitudinal axis 115 and defines a bore 118 extending therethrough. The distal termination 112b of introducer 110 can be sharp for tissue penetration, as shown in FIGS. 2 and 3. In another embodiment, the introducer 110 can have a rounded distal end for introduction through a body passageway or lumen, such as an elongate catheter for endoluminal introduction. In another embodiment (not shown), an introducer portion may not be needed and the energy delivery member 120 (FIG. 4) of the invention can be used independently, for example in a needle-type probe for percutaneous access to targeted tissue site.

In the exemplary embodiment of FIGS. 2 and 3, the energy delivery member 120 corresponding to the invention comprises an element that is extendable from the distal end 112b of the introducer portion for contacting tissue. The energy delivery member 120 typically has a working end 122 with a sharp distal termination 123 for tissue penetration as shown in FIG. 3, but it should be appreciated that other embodiments of the inventive working end and working surface are possible to delivering energy to tissue in contact with the working end-whether the targeted tissue is subsurface tissue or surface tissue.

More in particular, referring to FIG. 3, the working end 122 of the energy delivery member defines an exterior engagement surface or engagement plane 125 that contacts and delivers energy to a targeted tissue. For example, FIG. 4 generally depicts a sectional view of a tissue mass with a targeted tumor tissue it therein. The working end 122 is inserted through the targeted tissue tt that is below the surface s of the organ or skin. For example, the tumor tissue can reside in a patient's liver. In this embodiment, the cross-section of the energy delivery member 120 is round and is formed as a needle having a diameter ranging from about 0.05" to 0.25". It should be appreciated that the energy delivery member 120 can have any other cross-sectional shape, such as oval or rectangular shape.

In the exemplary embodiment of FIG. 3, the engagement surface or plane 125 that delivers energy to tissue extends an axial length L (from proximal surface end 126a to distal surface end 126b) along the member 120 as well as 360.degrees around the circumference of the member. The dimensions of the engagement surface or plane 125 can comprise the entire exposed surface of the working end 122 or any radial portion thereof or a plurality of radial or axial portions thereof. As one example, the engagement plane 125 can comprise only one surface on one side of the member 120 (see FIGS. 8–10A).

Figure 5:
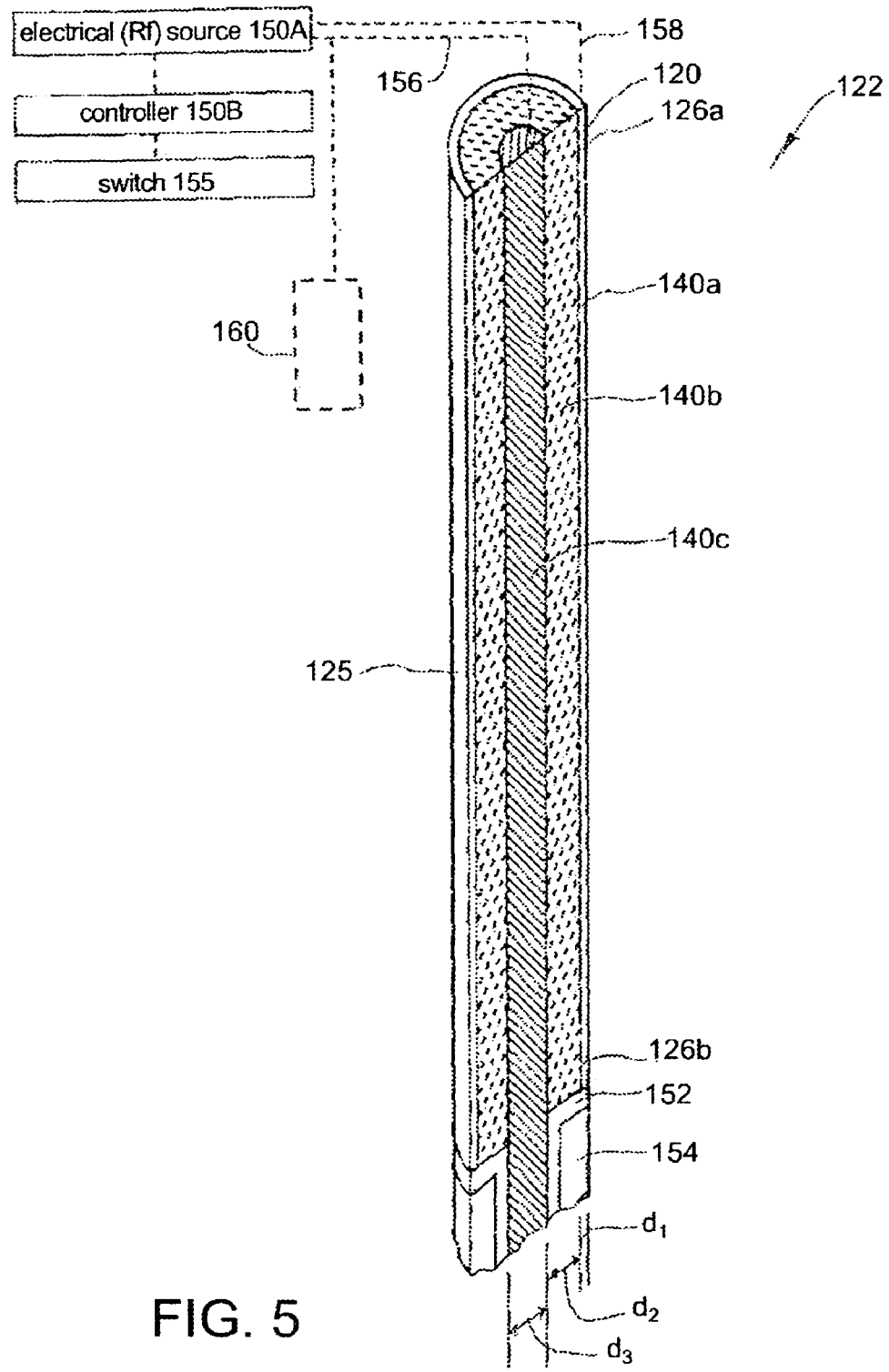
FIG. 5 is a sectional view the working end of the probe of FIG. 3 taken along line 5—5 of FIG. 3 showing the components of the energy delivery member.

The sectional view of FIG. 5 more particularly illustrates the working end components of the invention for controllably delivering energy to tissue. The engagement surface or plane 125 of working end 122 is fabricated of a (first) conductive surface or material indicated at 140A that is both electrically conductive and thermally conductive and can be any suitable material known in the art (e.g., gold, platinum, palladium, silver, stainless steel, etc.). As shown in FIG. 5, the first conductive surface 140A can have any suitable thickness dimension $d_1$ and can comprise a thin-wall sleeve or alternatively a thin film deposit in the order of 0.001" to 0.005" on member 120, or in some cases can simply comprise a surface layer portion of the next described interior layer 140B.

As can be seen in FIG. 5, an interior of working end 122 carries a medial (second) conductive material or layer indicated at 140B and an inner (third) conductive material or electrode 140C at a core of the member 120. Each of the medial and inner conductive layers, 140B and 140C, has any suitable cross-sectional dimension indicated at $d_2$ and $d_3$, respectively. Preferably, the cross-sectional dimension of the medial (second) conductor 140B and inner (third) conductor 140C comprise a substantial fraction of the mass of the working end 122 to provide a thermal mass for optimizing passive conduction of heat to tissue as will be described below. The innermost or third conductive material 140C at the core of member 120 comprises an electrical conductor (or electrode) and is coupled by an electrical lead to a remote Rf source 150A and optional controller 150B. It can be further understood from FIG. 5 that the inner (third) conductive material 140C is coupled to, or immediately adjacent to, the medial (second) conductive material 140B for conducting electrical energy from the core third material 140C to the adjacent second material 140B. Likewise, the medial (second) conductive material 140B is in contact with the outer (first) conductive material 140A.

FIG. 5 further illustrates that shows that the proximal end 126*a* and distal end 126*b* of the engagement surface 125, as well as the medial conductive material 140B, are spaced apart from the core (third) conductive material 140C by an insulator material 152 (see also FIG. 3). Thus, the member 120 can only conduct electrical energy to the engaged tissue via conductive layers 140C, 140B and through the engagement surface 125. The body portions 154 of the member 120 thus cannot conduct electrical energy to tissue and preferably are a portion of an insulative body to prevent substantial thermal conduction therethrough.

Of particular interest, still referring to FIG. 5, the medial (second) conductive material indicated at 140B comprises a polymeric material or matrix having a resistance (i.e., impedance to electrical conduction therethrough) that changes in response to its temperature. Such materials are typically known in the art as polymer-based temperature coefficient materials, and sometimes specifically described as thermally sensitive resistors or thermistors whose characteristics exhibit very large changes in resistance with a small change of body temperature. This change of resistance with a change in temperature can result in a positive coefficient of resistance where the resistance increases with an increase in temperature (PTC or positive temperature coefficient material). The scope of the invention also includes medial conductive material 140B (see FIG. 5) of a negative temperature coefficient (NTC) material wherein its resistance decreases with an increase in temperature.

Figure 6:
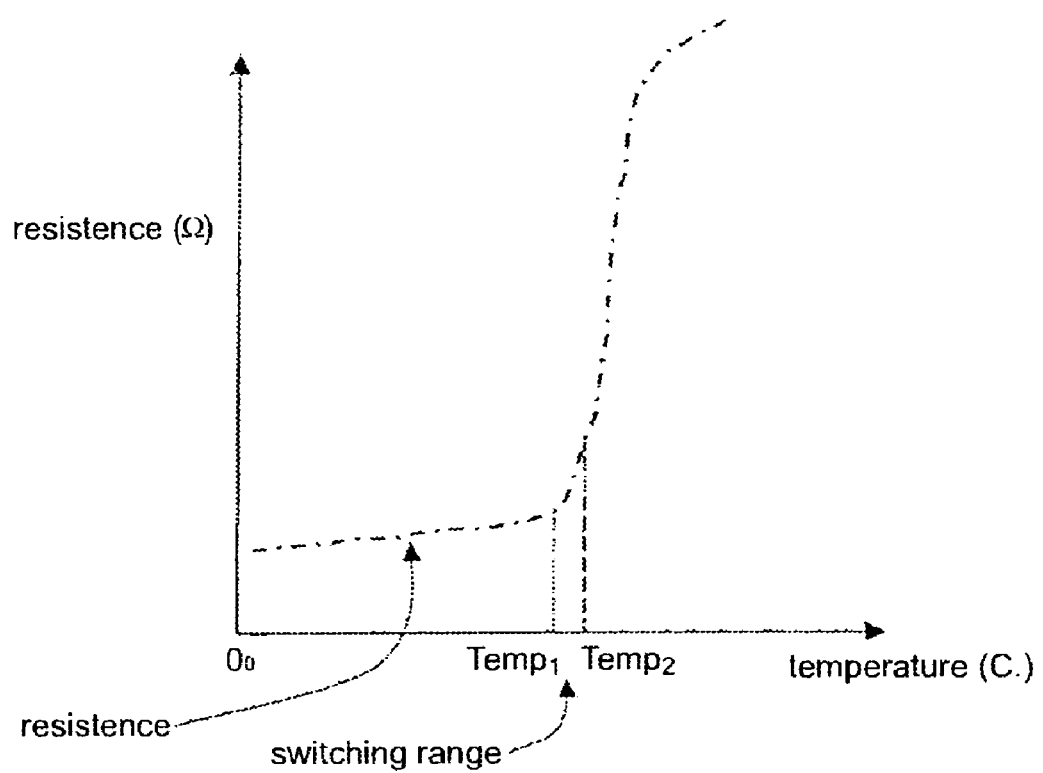
FIG. 6 is a graph of the temperature vs. resistance profile of the positive temperature coefficient material of the energy delivery member of FIG. 5.

In one type of PTC material, a ceramic PTC layer can be engineered to exhibit unique resistance vs. Temperature characteristics that can maintain a very low base resistance over a wide temperature range, with a dramatically increasing resistance (i.e., several orders of magnitude) above a specific temperature of the material which is sometimes referred to as a Curie point or switching range as illustrated in FIG. 6. As will be described below, one purpose of the invention is to fabricate the medial conductive material 140B (see FIG. 5) to have a selected switching range between a first temperature ($Temp_1$) and a second temperature ($Temp_2$) that approximates the targeted tissue temperature in the contemplated thermally-mediated therapy. The selected switching range, for example, can be any substantially narrow 2–5° C. range within the broader hyperthermia field (e.g., 45–65° C.) or the ablation field (e.g., 65–200° C.). It can be understood that the engagement plane 125 will cause the application of active Rf energy to tissue in contact therewith, and proximate thereto, until the medial conductive layer 140B is heated to the selected switching range. Thereafter, the mass of the working end 122 is elevated to a temperature at or above the selected switching range and will thereafter conduct or radiate thermal effects to the engaged tissue.

Thus, the critical increase in temperature of medial second conductive material 1401B is typically caused by the transient high temperature of tissue that is caused by active Rf heating of the tissue. In turn, heat is conducted back through the layer of the first conductive material 140A to medial conductive material 140B. (Another embodiment below describes the use of direct electrical current flow to thus cause internal heating of the medial conductive material 140B, see FIG. 24). A suitable PTC material can be fabricated from high purity semi-conducting ceramics, for example, based on complex titanate chemical compositions (e.g., $BaTiO_3$, $SrTiO_3$, etc.). The specific resistance-temperature characteristics of the material can be designed by the addition of dopants and/or unique materials processing, such as high pressure forming techniques and precision sintering. Suitable PTC materials are manufactured by a number of sources, and can be obtained, for example from Western Electronic Components Corp., 1250-A Avenida Acaso, Camarillo, Calif. 93012. Another manner of fabricating the medial conductive material 140B is to use a commercially available epoxy that is doped with a type of carbon. In fabricating a substantially thin medial conductive layer 140C in this manner, it is preferable to use a carbon type that has single molecular bonds. It is less preferred to use a carbon type with double bonds.

As can be seen in FIG. 5, the third conductive material or electrode 140C at the core of member 120 is operatively connected to the Rf source 150A by a first electrical lead 156 that defines a first polarity of the Rf source. In this preferred embodiment, the conductive engagement surface 140A is coupled to a second electrical lead 158 that defines a second or opposing polarity of the Rf source 150A. A ground pad indicated at 160 in FIGS. 4 and 5 also is coupled to the first lead 156 to accomplish a preferred method of the invention, as will be described below.

Figure 1A:
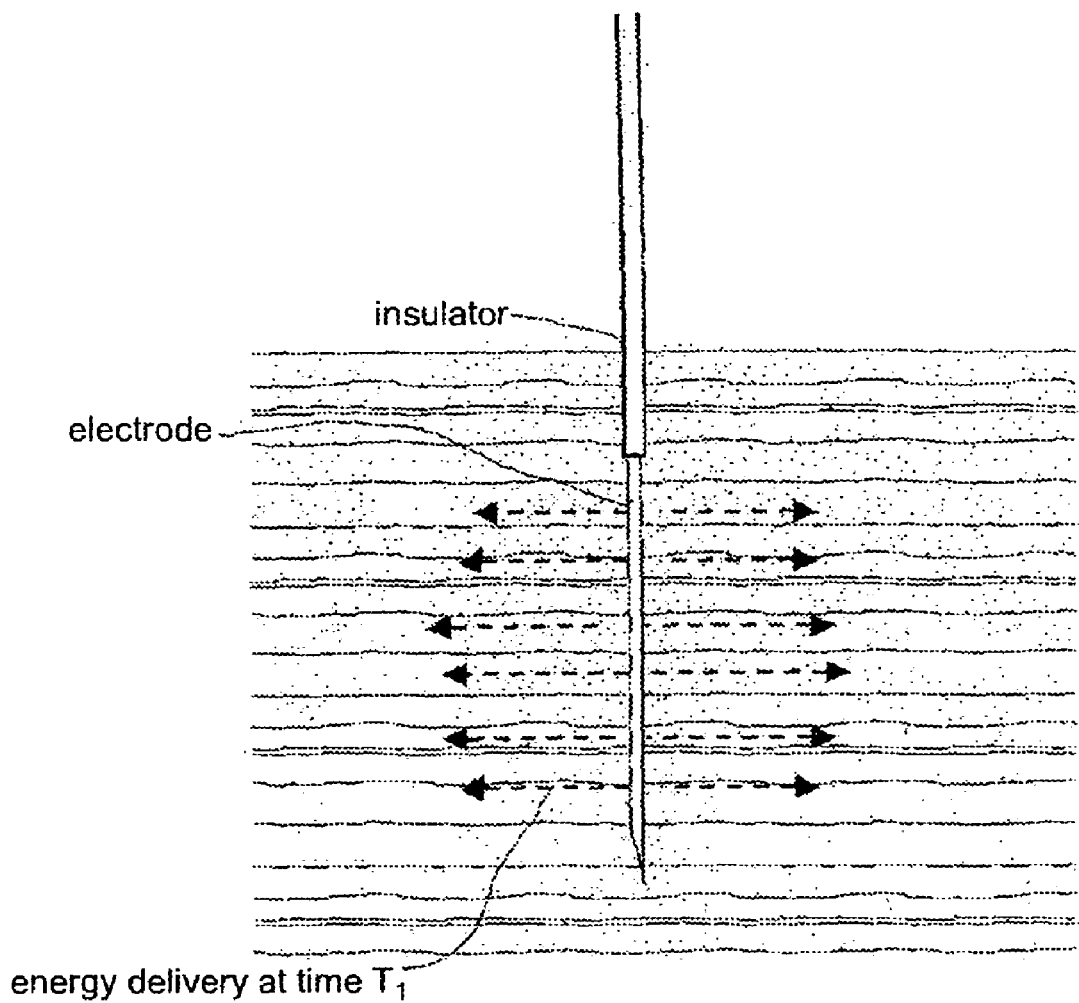
FIG. 1A is a cross-sectional view of a prior art Rf needle apparatus illustrating its method of developing an active Rf current density in tissue at the initiation of energy delivery, further showing exemplary isotherms caused by such energy delivery.
Figure 1B:
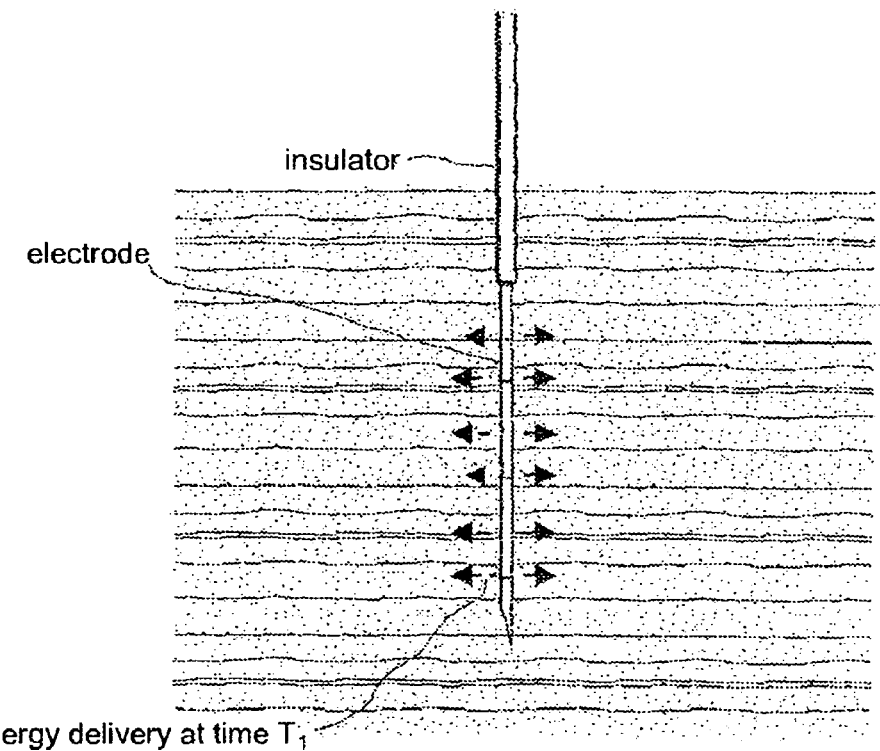
FIG. 1B is a cross-sectional view of the a prior art Rf needle of FIG. 1A after an arbitrary time interval showing reduced current density in tissue, further showing exemplary isotherms that result from increased tissue impedance about the needle.
Figure 7A:
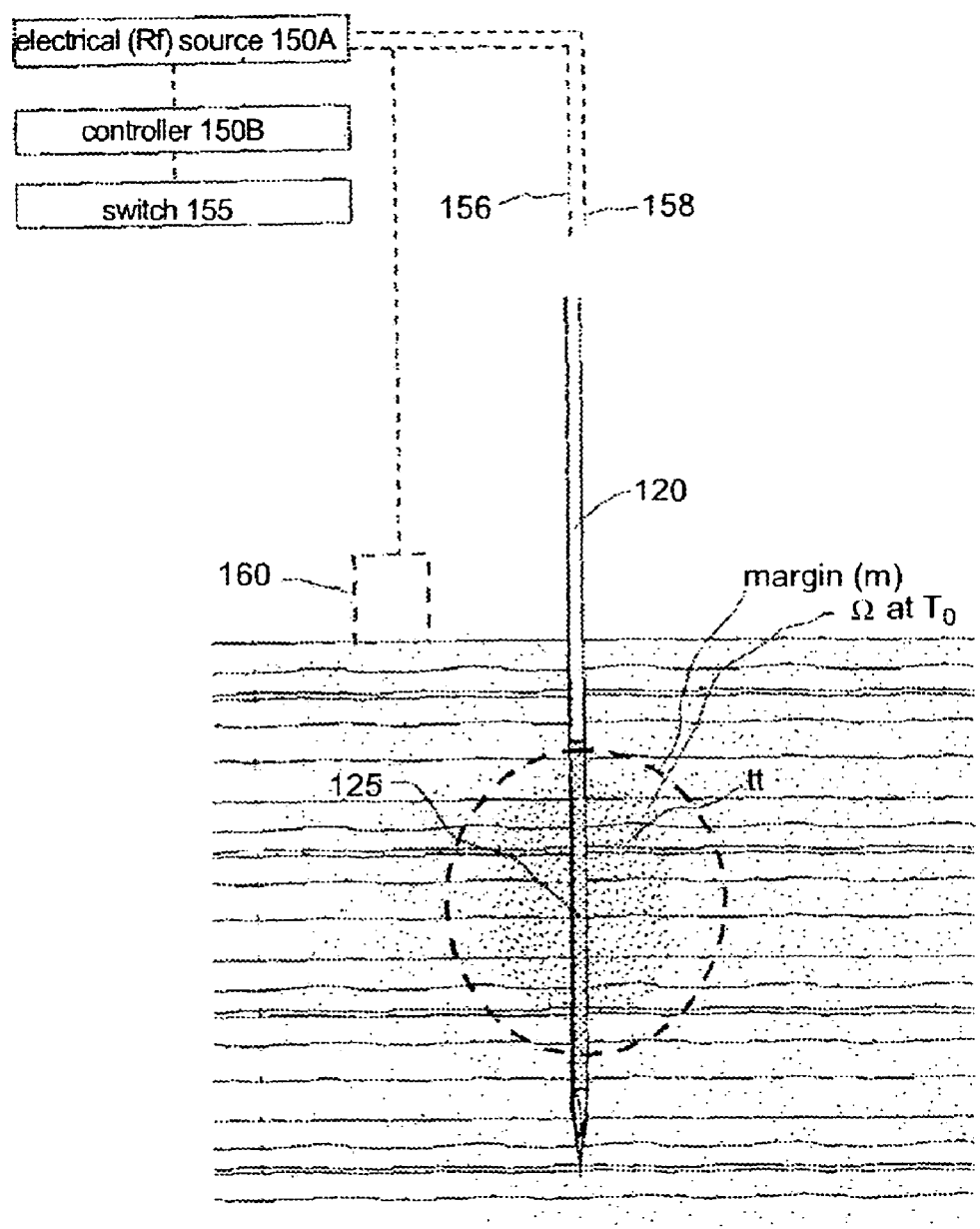
FIG. 7A is a sectional view of a tissue mass and a tumor with the working end of the probe of FIG. 2 positioned therein.
Figure 7B:
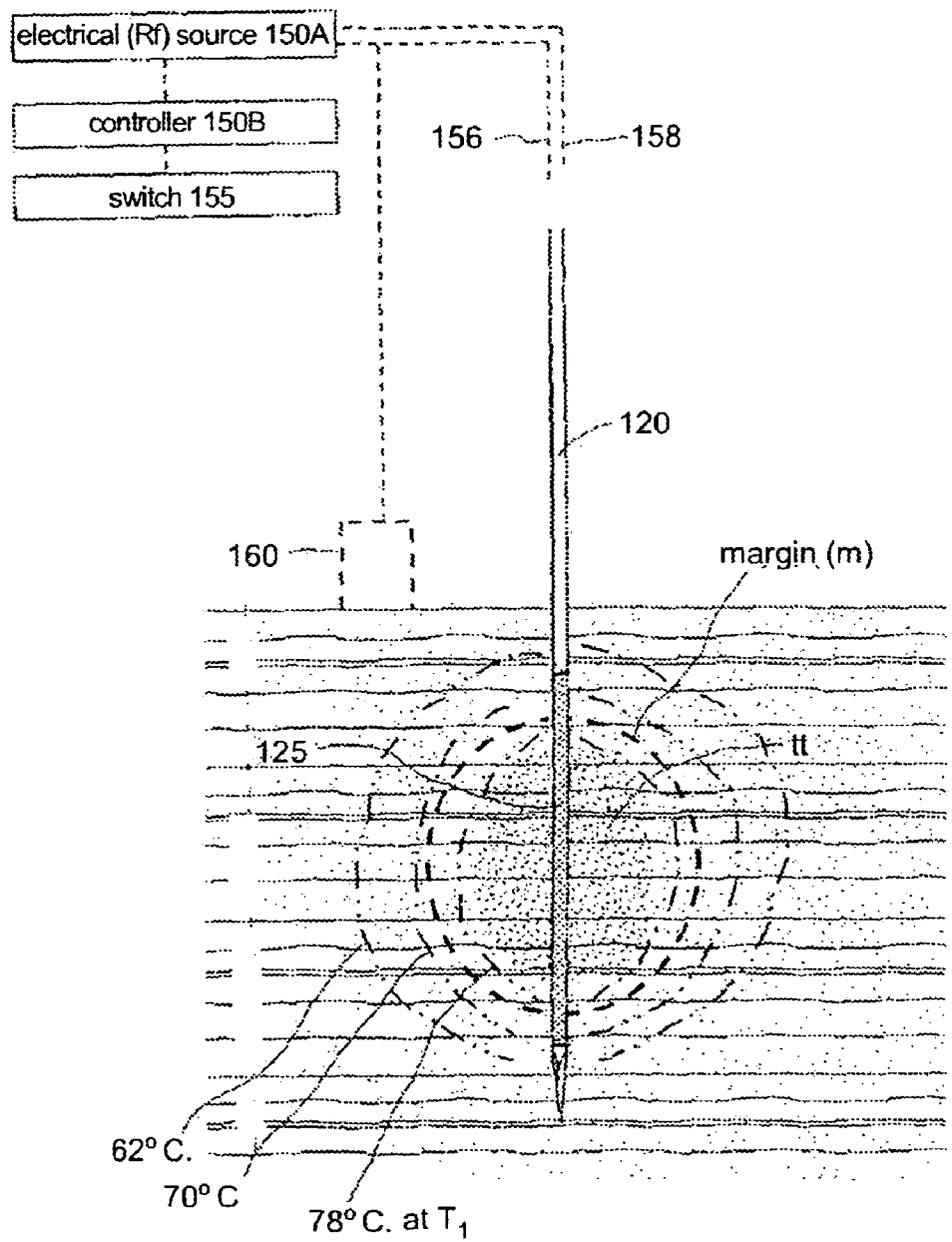
FIG. 7B is a sectional view of a tissue mass similar to FIG. 7A showing isotherms in the method of treatment with the probe of FIGS. 1–5.

2. Method of use of Type "A" embodiment. Referring to FIGS. 7A–7B, the manner of utilizing the probe 100 of FIG. 1 to perform a method of the invention is illustrated. FIG. 7A illustrates a tumor tissue tt targeted for hyperthermic treatment or ablation. For example, the targeted tissue tt can be a tumor in a patient's liver wherein the thermally-mediated therapy is defined by the delivery of a thermal energy dose that comprises (i) a minimum selected temperature across the targeted tissue tt, and (ii) the maintenance of the selected temperature of a selected time interval. As an example, consider that the parameters of a therapy is to deliver a minimum of 70° C. for 600 seconds to the targeted tissue including margins m, although the temperature and duration for a particular therapy can be any suitable parameters ranging from about 40 to 200° C. for from about 10 seconds to 20 minutes.

In the exemplary procedure, the physician selects a working end that carries a medial conductor matrix 140C (see FIGS. 5 and 6) that has a switching range at or about 70° C, or more particularly a conductor matrix 140C that increases in resistance by a factor of 100 or more from its low base resistively (see FIG. 6) as its temperature moves in a narrow switching range from about 68 to 72° C.

As can be understood from FIG. 7A, any overlying tissue such as an abdominal wall can be is penetrated by any suitable means such as a trocar that leaves a cannula (not shown) in place. Ultimately, the working end 122 of the energy delivery member or body 120 is placed in a desired relationship to the targeted tissue tt in a predetermined location, for example through the center of the targeted tissue tt as depicted in FIG. 7A The cross-section of the energy delivery member 122 can be equivalent to a needle, with any size in the range of about 30 to 12 gauge. A suitable imaging system is first used to define the volume of the targeted tissue tt and thereafter to localize the engagement surface 125 relative to the tumor. The length dimension L of the engagement surface 125 is selected to provide a suitable pattern for volumetric ablation of the targeted tumor tissue tt. The types of suitable imaging systems include, but are not limited to, ultrasound imaging, computerized tomography (CT) scanning, x-ray fluoroscopy, magnetic resonance imaging (MRI), and the like. The methods of using such systems to define the targeted tissue volume and localization of the engagement surface 125 are well known to those skilled in the art. For use in some imaging systems, the proximal, distal or other perimeters of the engagement surface 125 can carry imaging-sensitive markings (not shown).

After the targeted volume tt is well imaged, as illustrated in FIG. 7A, the method then can further define a certain margin m surrounding the tumor that is targeted for the ablative treatment. The working end 122 is introduced to the desired position as depicted in FIG. 7A. With the engagement plane 125 in contact with the targeted tissue, (at time $T_0$), the operator actuates a switch 155 that delivers Rf energy from the radiofrequency generator or source 150A to the core conductive element or electrode 140C. At ambient tissue temperature, the low base resistance of the medial conductive matrix 140B allows unimpeded Rf current flow from the source 150A through the engagement surface 125 and tissue to return electrical lead 158 that is coupled to ground pad 160. In FIG. 7A, it can be understood that the engaged tissue tt that is in contact with the engagement surface 125 initially will have a substantially uniform impedance (indicated at particular resistance level $\Omega$) to electrical current flow, which resistance $\Omega$ could increase substantially in proximity to the engagement surface 125 of the contacted tissue is overly dehydrated by the active Rf delivery.

After the initial activation of energy delivery at time To as depicted in FIG. 7A, the Rf current will create a certain energy density (or active Rf energy application) in the targeted tissue. Following an arbitrary interval indicated at time $T_1$ in FIG. 7B, the tissue's impedance proximate to engagement surface 125 typically will be elevated to a somewhat higher impedance level due to dehydration. However, at time $T_1$ in FIG. 7B, the active Rf energy application that elevates the tissue temperature will instantly conduct heat to the working end 122, including the PTC conductive layer 140B. Thus, it can easily be understood that when the tissue temperature and the temperature of the medial PTC conductive layer 140B reaches the level of the switching range (i.e., 68.to 72° C.), the Rf current flow from the core conductive electrode 140C to the engagement surface 140A will be substantially reduced or terminated due to the exponential increase in the resistance of medial conductor material 140B (see FIG. 6). It is believed that such an instant and automatic reduction of Rf energy application will prevent any substantial dehydration of tissue proximate to the engagement plane 125. By thus maintaining the desired level of moisture around the engagement plane 125, the working end can more effectively apply energy to the tissue—and provide a deeper thermal effect than would be possible with prior art Rf needles that can cause an irreversible dehydration (impedance increase) about the working end.

Still referring to FIG. 7B, as the tissue temperature proximate to engagement surface 125 falls by thermal relaxation in the tissue and lack of an Rf energy density, the temperature of the medial conductor 140B will thus fall below the threshold of the selected switching range. This effect then will cause Rf current to again flow through the assembly of conductive layers 140C, 140B and 140A to the targeted tissue to again increase the tissue temperature by active Rf heating of the tissue. The thermal relaxation in the tissue can be highly variable and is most greatly affected by blood flow, which subtracts heat from the tissue. In hypervascularized tumor tissue, such thermal relaxation is increased in speed.

By the above described mechanisms of causing the medial conductive matrix 140B to hover about its selected switching range, the actual Rf energy density in the tissue tt thus can be precisely modulated to maintain the desired temperature. FIG. 7B illustrates exemplary isotherms that can be maintained over any selected period of time to ablate the tumor and the desired tissue margins m. Of particular interest, the polymer matrix that comprises the medial conductor portion 140B is doped with materials to resistively heat the matrix as Rf energy flow therethrough is reduced. Thus, the thermal mass of the working end 122 is elevated in temperature to thereby deliver energy to the targeted tissue tt by means of greater passive conductive heating—at the same time Rf energy delivery causes lesser tissue heating. This balance of active Rf heating and passive conductive (or radiative) heating can maintain the targeted temperature for any selected time interval.

In summary, one method of the invention comprises the delivery of Rf energy from an Rf source 150A to a conductive engagement surface portion 140A of a probe through a thermally sensitive resistor material (medial layer 140B) wherein the resistor material has a selected switching range that approximates a targeted temperature of the therapy. In operation, the working end automatically modulates active Rf energy density in the tissue as the temperature of the engaged tissue conducts heat back to the thermally sensitive resistor material 140B to cause its temperature to reach the selected switching range. In this range, the Rf current flow will be reduced, with the result being that the tissue temperature can be maintained in the selected range without the need for thermocouples or any other form of feedback circuitry mechanisms to modulate Rf power from the source. Most important, it is believed that this method of the invention will allow for more immediate modulation of actual energy application to tissue than provided by a temperature sensor. Such temperature sensors suffer from a time lag. Further, a temperature sensor provides only an indirect reading of actual tissue temperature-since a typical sensor can only measure the temperature of the electrode.

Another method of the invention comprises providing the working end with a suitable cross-section of thermally resistive matrix 140B so that when it is elevated in temperature to the switching range, the conductive matrix 140B effectively functions as a resistive electrode to passively conduct thermal energy to engaged tissue. Thus, in operation, the working end 122 can automatically modulate the application of energy to tissue between active Rf heating and passive conductive heating of the targeted tissue at a targeted temperature level.

Figure 7C:
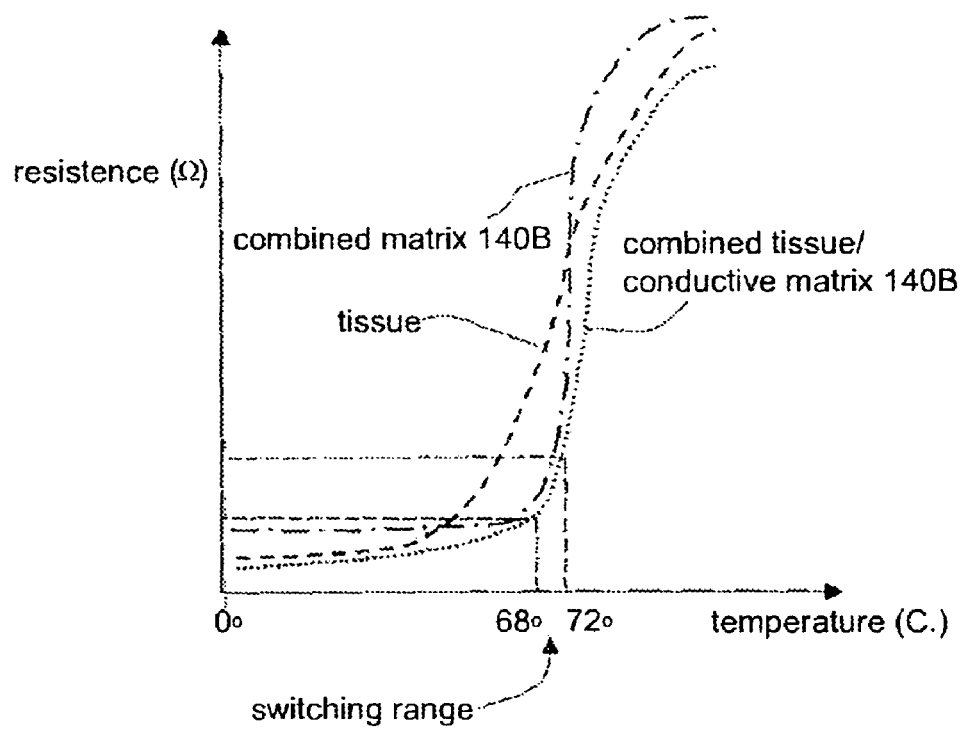
FIG. 7C is a graph showing the temperature-resistance profile of the medial conductive layer of the probe of FIGS. 1–5.

FIG. 7C illustrates another aspect of the method of the invention that relates to the Rf source 150A and controller 150B. A typical commercially available radiofrequency generator has feedback circuitry mechanisms that control power levels depending on the feedback of impedance levels of the engaged tissue. FIG. 7C is a graph relating to the probe of present invention that shows: (i) the temperature-resistance profile of the targeted tissue, (ii) the resistance-resistance profile of the PTC conductive matrix 140B of the probe, and (iii) the combined resistance-resistance profile of the tissue tt and the PTC conductive matrix. As can be understood from FIG. 7C, in operation, the Rf source 150A and controller 150B can read the combined impedance of the tissue tt and the PTC conductive layer which will thus allow the use of the instrument with any typical Rf source without interference with feedback circuitry components.

Figure 8:
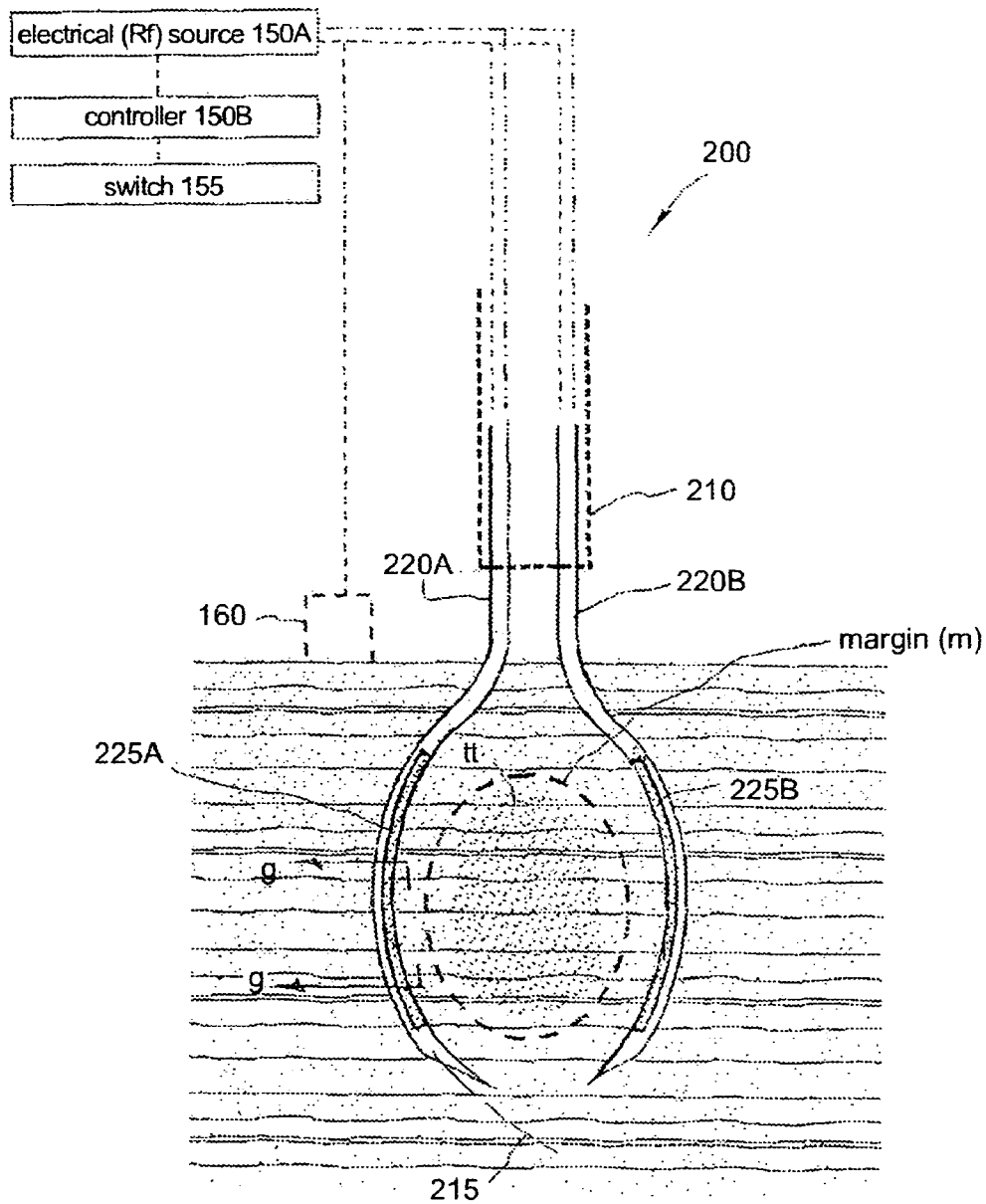
FIG. 8 is a schematic view of a Type "B" probe in accordance with the invention with a positive temperature coefficient conductive material that is flexible or compressible and illustrated in a probe having a plurality of energy delivery members that can be deployed on opposing side of a targeted tissue.

3. Type "B" probe for energy delivery to targeted tissue. An exemplary Type "B" probe 200 corresponding to the invention is illustrated in FIG. 8 that is adapted for energy delivery to tissue and again is described in treating a targeted benign or malignant tumor. The probe 200 includes a proximal handle (not shown) coupled to an introducer portion 210 that can carries at least one extendable energy delivery member. In the exemplary embodiment of FIG. 8, the probe 200 carries a plurality of energy delivery members 220A–220B which can number from two to 8 or more. For convenience, the probe of FIG. 8 depicts two members 220A–2201B that define respective engagement planes 225A–225B.

One principal difference between the Type "B" probe and the previously described Type "A" probe is that a Type "B" energy delivery member is (i) substantially flexible in bending, or (ii) resilient in a radial direction relative to the axis 215 of the member. One purpose for flexible energy delivery members 220A–220B is so that the members can fan out to surround the targeted tissue tt as they are advanced out of introducer 210 in a somewhat lateral direction relative to the longitudinal axis of the introducer 210. The deployed energy delivery members 220A–220B can have a variety of different deployed geometries including one or more radii of curvature. As shown in FIG. 8, the energy delivery members 220A–220B in a deployed position have a curved portion that can define a volume of targeted tissue therebetween that is targeted for ablation. As can be easily understood, prior to deployment, the energy delivery members 220A and 220B of FIG. 8 can be constrained in a linear position in channels in the introducer 210. Typically, the interior cores of the members 220A–220B are of a spring-type material or shape-memory material that is tensioned when confined in a channel of the introducer 210. The members 220A and 220B become sprung or expanded as the members are deployed and extended from the introducer 210. Alternatively, the energy delivery members can be made of a shape memory metal (e.g., a nickel titanium alloy) as is known in the art to thereby provide an expanded shape outside of the introducer following a change in temperature caused by resistive heating thereof.

Figure 9:
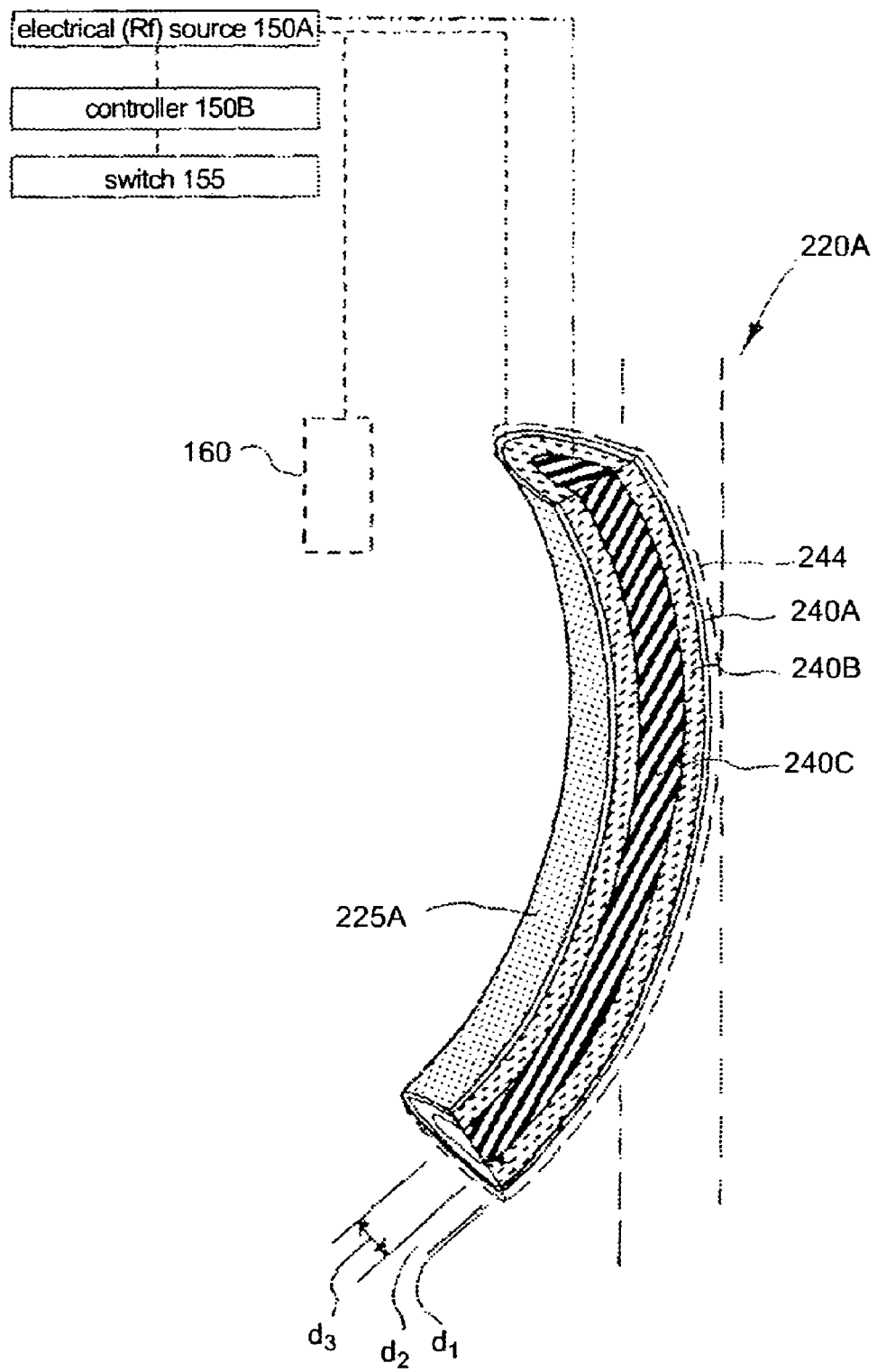
FIG. 9 is a sectional view of a portion of one of the energy delivery members of the probe of FIG. 8 taken along line 9—9 of FIG. 8 rotated 90 degrees showing the component portions thereof.

Of particular interest, the requirement of a flexible or resilient energy delivery member resulted in the development of an assembly of materials that provide a flexible or resilient surface engagement layer portion 240A, a flexible or resilient medial conductive portion 240B of a PTC-type material together with a core conductive portion (electrode) 240C of a shape memory or spring-type material. FIG. 9 illustrates an exemplary section of such a flexible energy delivery member 220 that can bend to a straight position indicated in phantom view. The core conductive electrode 240C again is coupled to electrical source 150A and controller 150B, as described previously.

The energy delivery member 220 of FIG. 9 has a core conductor 240C that can be oval and is of a shape memory material of any suitable dimension indicated at $d_3$. Of particular interest, the medial conductive portion 240B comprises a silicone material that can function as a PTC-type resistive matrix that functions as described above. More in particular, one embodiment of the medial conductive portion 240B can be fabricated from a medical grade silicone. The silicone material of the medial conductive portion 240B was doped with a selected volume of conductive particles, e.g., carbon or graphite particles. By weight, the ration of silicone-to-carbon can range from about 10/90 to about 70/30 (silicone/carbon) to provide various selected switching ranges wherein the inventive composition functions as a PTC material exactly as described previously. More preferably, the carbon percentage in the matrix is from about 40–80% wit the balance silicone. As described previously, carbon types having single molecular bond are preferred. One preferred composition has been developed to provide a switching range of about 75 to 80° C. with the matrix having about 50–60 percent carbon with the balance of silicone. The medial conductive portion 240B can have any suitable thickness dimension indicated at $d_2$, ranging from about 0.001" to 0.02" depending on the cross-section of member 220A, and it should be appreciated that such thickness dimension $d_2$ will increase substantially as its temperature increases which is a significant factor in its increase in resistance to current flow across the element (see FIG. 6). The embodiment of FIG. 9 further shows a substantially flexible surface engagement layer portion 240A. Such a thin flexible and/or stretchable coating can comprise any suitable thin-film deposition, such as gold, platinum, silver, palladium, tin, titanium, tantalum, copper or combinations or alloys of such metals, or varied layers of such materials. A preferred manner of depositing a metallic coating on the polymer element comprises an electroless plating process known in the art, such as provided by Micro Plating, Inc., 8110 Hawthorne Dr., Erie, Pa. 165094654. The thickness d, of the metallic coating ranges between about 0.0001" to 0.005". Other similar electroplating or sputtering processes known in the art can be used to create a thin film coating. As another alternative, spaced apart strips of a thin metallic foil can be bonded to the flexible substrate layer portion 240B[which thereby would comprise the engagement plane 240A.

Figure 10A:
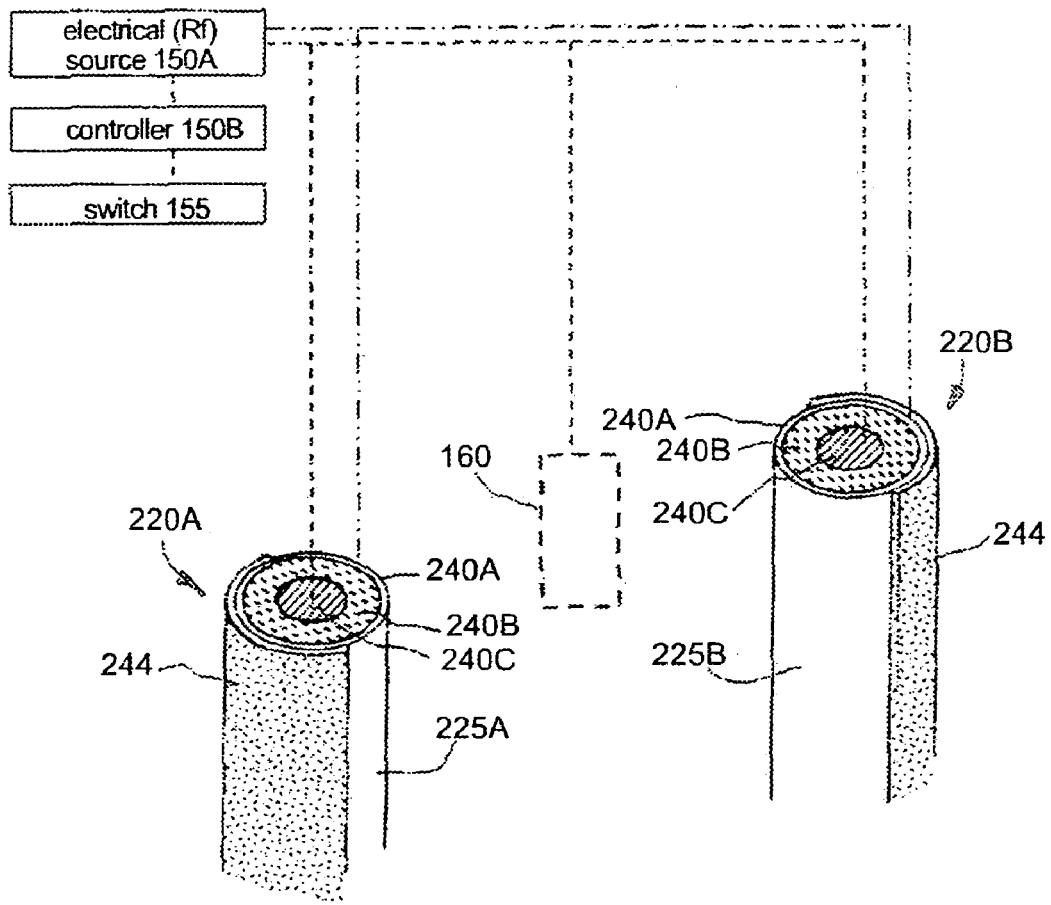
FIG. 10A is an enlarged sectional view of the working end of the probe of FIG. 8 illustrating the connection of multiple engagement planes to an RF source and controller.

In the probe of FIGS. 8 & 10A, it can be seen that the engagement planes 225A–225B are provided in a longitudinal arrangement on only one face of each member. The outwardly-facing portion of each member 220A–220B is covered with an insulator layer indicated at 244. The insulator layer 244 can be of any suitable material such as nylon, polyimide or many other thermoplastics. Such an insulator layer 244 is optional and is shown in phantom view in the sectional view of FIG. 9.

In operation, referring to FIGS. 8 and 10A, it can be seen that the energy delivery members 220A–220B can fan out to surround the targeted tissue tt as they are advanced out of the introducer in a somewhat lateral direction relative to the introducer axis. Assume that the therapy again involves the ablation of a benign or malignant tumor, including margins m around the exterior surface of the tumor. It can be easily understood that the plurality of engagement planes 225A–225B on opposing sides of the targeted tissue tt can help to confine the Rf energy density in the region circumscribed by the plurality of energy delivery members 220A–220B. The insulator layer 244 further prevents the active Rf heating of tissue outwardly from the members. In all other respects, the deployed energy delivery members 220A–220B function as described above to modulate energy application to the targeted tissue tt based on the selected switching range of the medial thermally-sensitive material 240B.

Figure 10B:
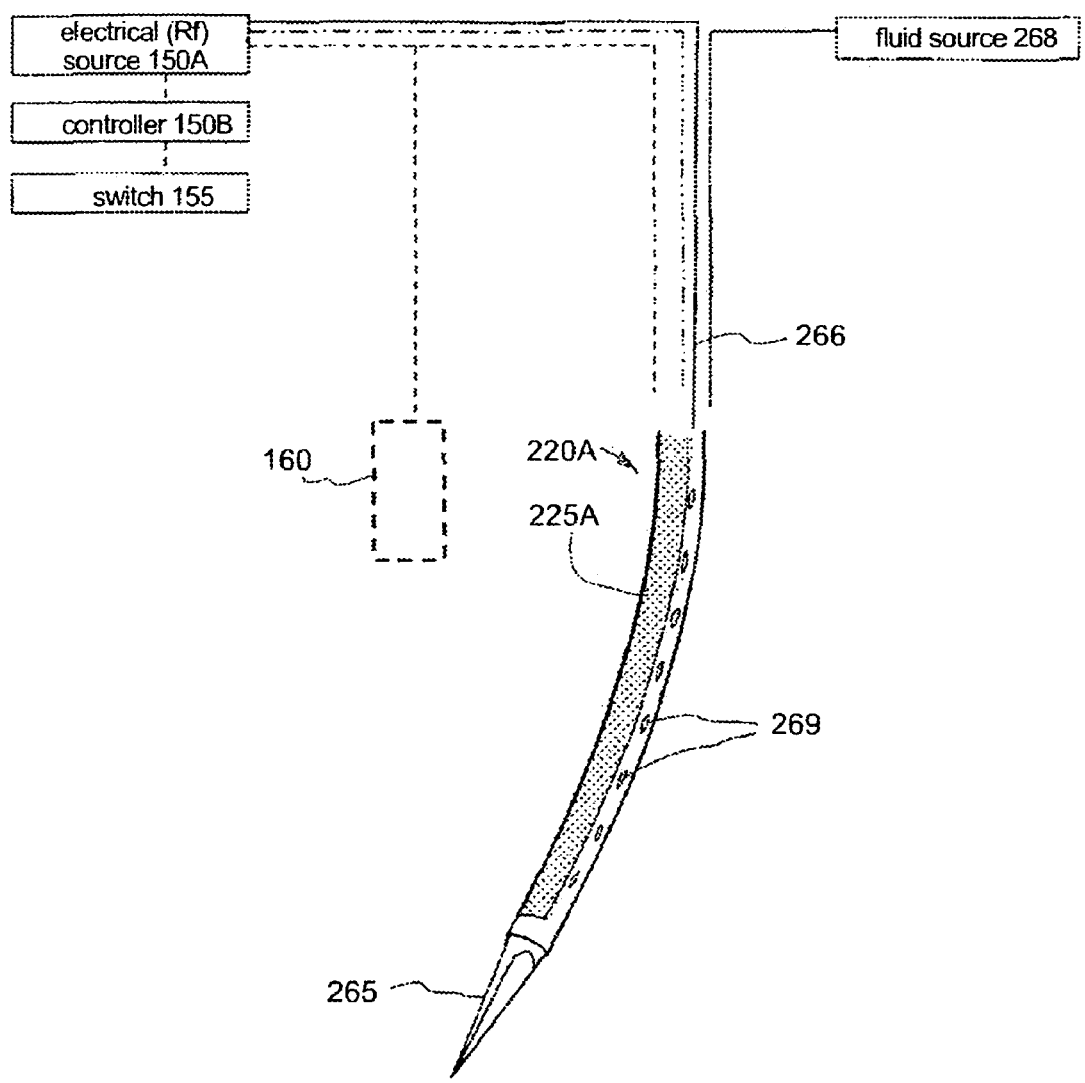
FIG. 10B is view of an alternative embodiment of the working end of the probe of FIG. 8 illustrating a cutting electrode at a distal tip of the energy delivery member and saline inflow ports proximate to the engagement plane.

FIG. 10B illustrates another embodiment of the energy delivery member 220A of FIG. 8. In this embodiment, the distal termination of member 220A carries an Rf cutting electrode 265 that is independently coupled to a high voltage Rf source. It can be understood that an insulated electrical lead 266 can run through the length of energy delivery member 220A. When the member 220A is piercing into tissue, the activation of such a high voltage electrode 265 as is known in the art can cause the tip to cut into tissue to thereby allow the shape memory member 220 to not deflect from its desired path. FIG. 10B illustrates another optional feature of an energy delivery member that comprises a saline inflow mechanism that comprises a remote saline source 268 and at least one inflow port 269 proximate to, or within, the engagement plane 225. In some thermally-mediated therapies, either the time duration of the therapy or the targeted temperature can cause unwanted dehydration that will reduce the application of energy to tissue, both active Rf heating and conductive heating as described above. An inflow of saline solution from source 268, either controlled by a pressure source coupled to controller 150B or a gravity system can maintain conductive fluid about the engagement plane of the working end. The size and number of fluid inflow ports 269 can vary, depending on the dimensions and shape of the engagement plane 225.

Figure 11A:
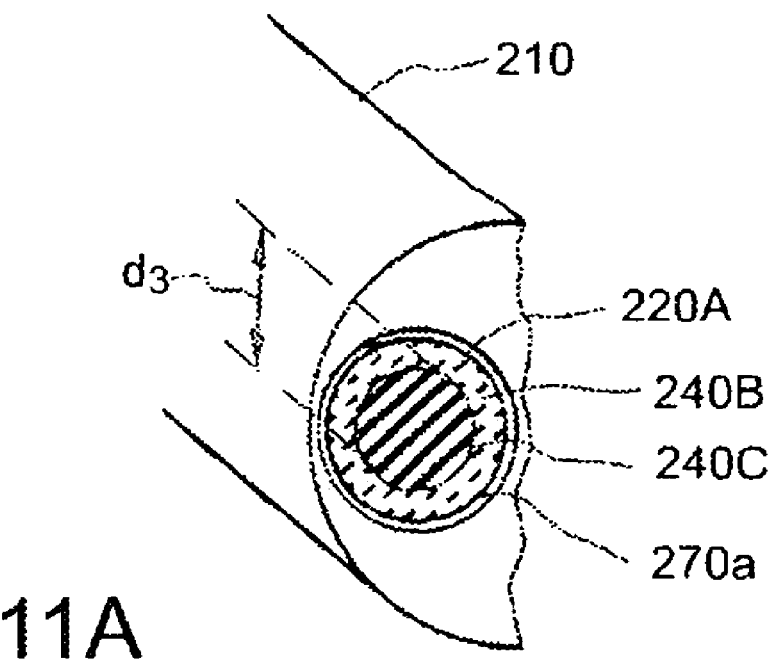
FIG. 11A is a sectional view of the working of an alternative Type "C" embodiment that illustrated an energy delivery member with a compressible engagement plane and underlying positive temperature coefficient conductive material in a pre-deployed position.
Figure 11B:
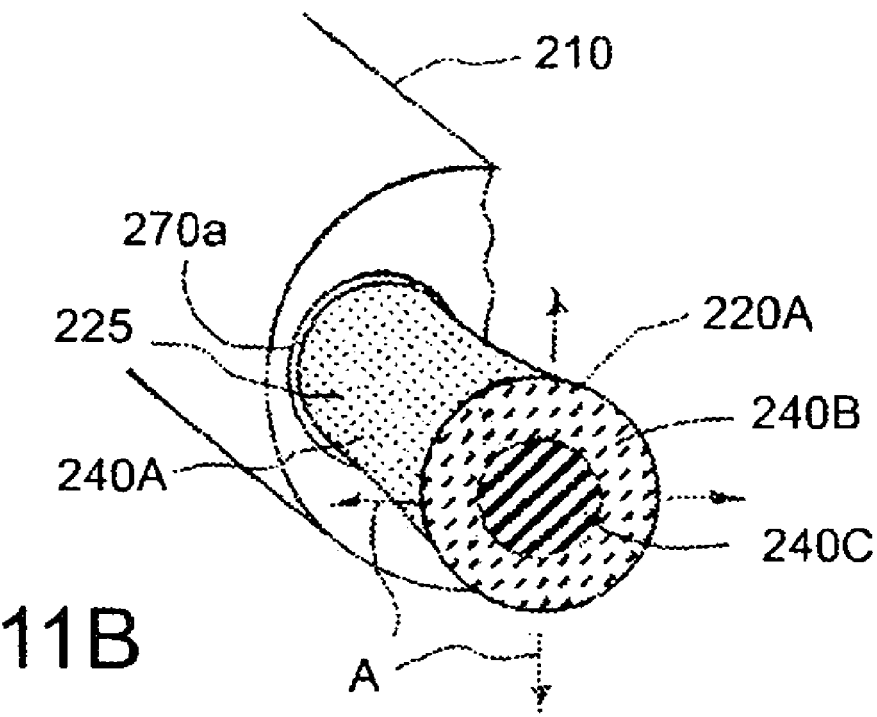
FIG. 11B is a sectional view of the probe of FIG. 11A illustrating the compressible engagement plane and underlying positive temperature coefficient conductive material in a deployed position.

As described above, the scope of the invention includes an energy delivery member 220A with a medial conductive layer 240B that is resilient, compressible or radially flexible. FIGS. 11A–11B illustrate an energy delivery member 220A that can comprise an alternative embodiment of the type of probe 200 described in FIGS. 8–10A FIG. 11A illustrates a cut-away view of introducer 210 that slidably carries a round energy delivery member 220A that again has a core conductor 240C having any suitable cross-sectional dimension $d_3$. The medial conductive portion 240B comprises a silicone material that functions as a PTC-type resistive matrix and also is somewhat compressible or spongy. The manufacture of such compressible or slightly spongy forms of silicone is known in the art, for example by introducing foams or bubbles into a silicone polymer during its formation. Thus, the medial conductive portion 240B can be compressed and constrained in channel 270a in the introducer as depicted in FIG. 11A. FIG. 11B depicts the slidable deployment of member 220A wherein its radial expansion is indicated by arrows A. In some embodiments, the deployment of the member 220A and expansion of medial conductive portion 240B may only expand the diameter of the member by a small percentage. However, in small cross-section members 220 that are percutaneously introduced, any increase in the surface area of the engagement plane 225 and surface conductive layer 240A can be very important. In the application of Rf energy to tissue, the effective area of the electrode surface is critical for energy delivery.

Figure 12:
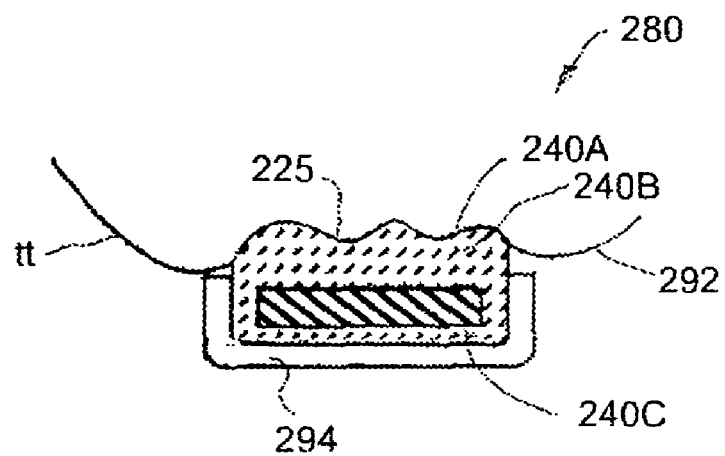
FIG. 12 is a sectional view of an alternative Type "C" energy delivery member with a compressible engagement plane illustrating it use in engaging an irregular surface of an anatomic structure.
Figure 13:
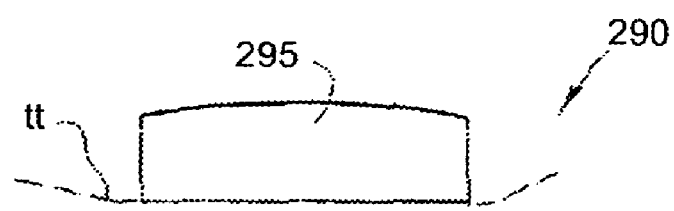
FIG. 13 is a sectional view of an alternative Type "C" energy delivery member with a compressible engagement plane illustrating it with a cooperating clamping mechanism.
Figure 13:
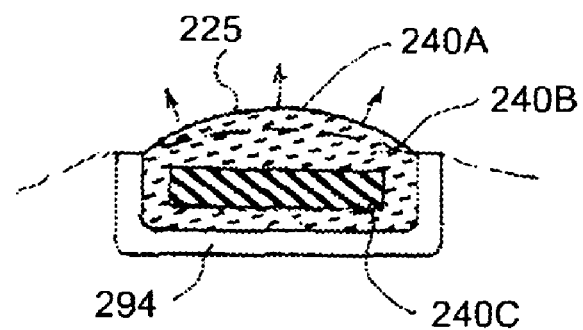

FIGS. 12 and 13 illustrate other embodiments of energy delivery members 280 and 290 that have a medial conductive portion 240B that is compressed to provide other advantages. These embodiments, in general, again have a core portion 240C that is coupled an Rf source 150A and further define a surface engagement plane 240A as described above for contacting the targeted tissue tt. As described above, the inventive energy delivery member can be used for any thermally-mediated therapy for any thermal dose and in some cases it may be desirable to apply energy about a surface of a substantially firm organ or anatomic structure 292. In such a case, as illustrated in FIG. 12, it would then be desirable to provide an engagement plane 225 conforms to the surface contours of the anatomic structure 292 that is engaged to thereby provide more effective energy delivery. In FIG. 12, the portion of the energy delivery member shown has an insulator layer 294 about three sides of the member to provide an engagement plane 225 extending along one side of the member. FIG. 13 illustrates another embodiment of energy delivery member 290 that can benefit from a compressible or resilient engagement plane 225. In this embodiment, the engagement plane 225 can again form one surface of a member and cooperates with a clamping member 295 that clamps the targeted tissue tt against the plane 225. In other words, the engagement plane can be carried by either or both elements of a jaw structure. In operation, the resiliency of the medial conductive portion 240B can optimally maintain the engagement plane 225 in suitable engagement with the surface of the targeted tissue as the characteristics of the tissue are changed, for example by dehydration, wherein the engagement plane will expand as the tissue shrinks (see arrows in FIG. 13). When applying a thermally-mediated therapy for purposes of coagulation or sealing, the tissue can be expected to dehydrate and shrink to some extent.

In another embodiment, the variably resistive matrix can be a pressure-sensitive resistive material that is carried in an exterior layer or body portion at an exterior of a probe working end. For example, the variably resistive layer can be substantially thin and fabricated of a material called a "pressure variable resistor ink" identified as Product No. CMI 118-44 available from Creative Materials Inc., 141 Middlesex Rd., Tyngsboro, Mass. 01879. The resistance vs. pressure characteristics of the variably resistive matrix can be adjusted by blending with Product No. CMI 117-34 that is available from the same source. It can be appreciated that the working end of the probe can function somewhat as depicted in FIGS. 12 and 13 wherein increasing pressure against the pressure-sensitive resistive layer can decrease its resistance to enhance Rf application to tissue through the layer. Conversely, the pressure-sensitive resistive layer can be of a type that increases in resistance as pressure is applied thereto. Such a pressure-sensitive resistive material further can be an open cell of a closed cell sponge-type material. In another embodiment, the system can provide a fluid source coupled to the open cell variably resistive material to provide fluid flows thereto as will be described further below.

Figure 14:
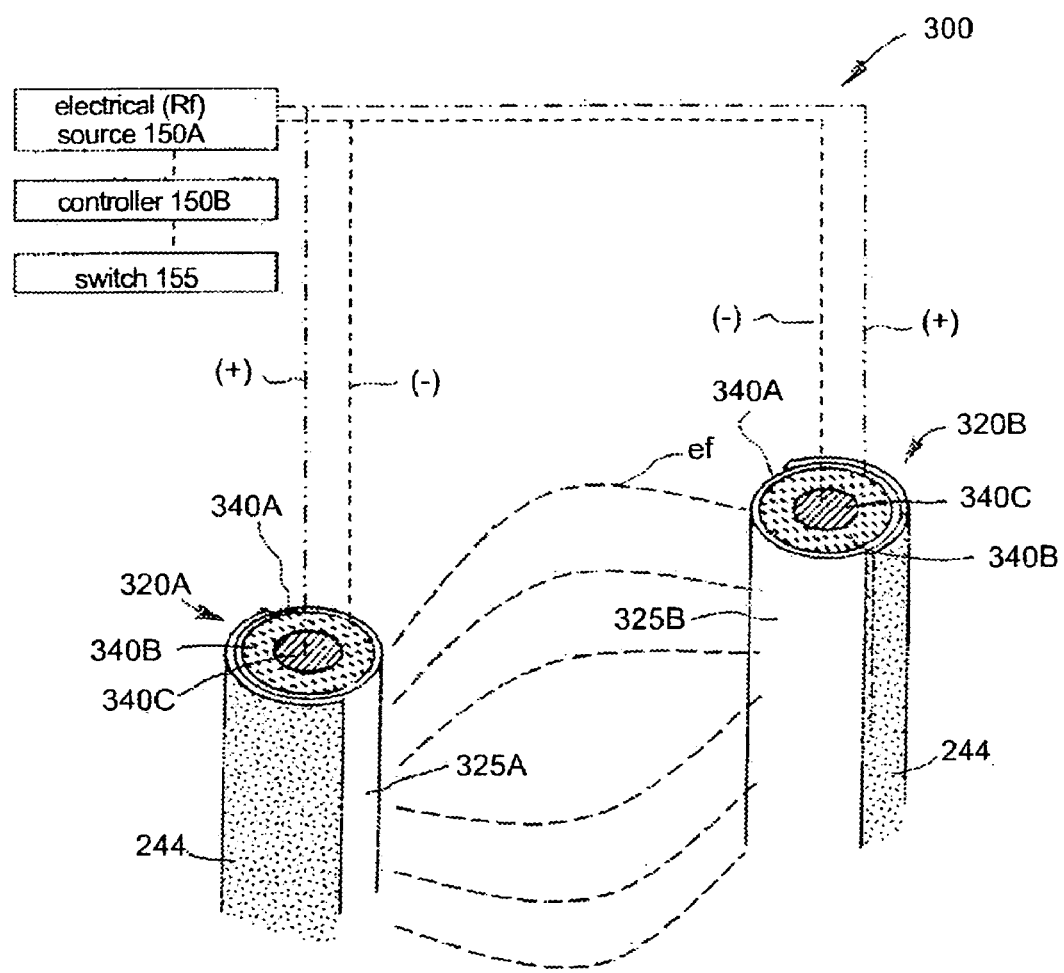
FIG. 14 is a sectional view of a Type "C" probe that similar to the probe of FIG. 8 except for providing a bi-polar mode of operation.
Figure 15A:
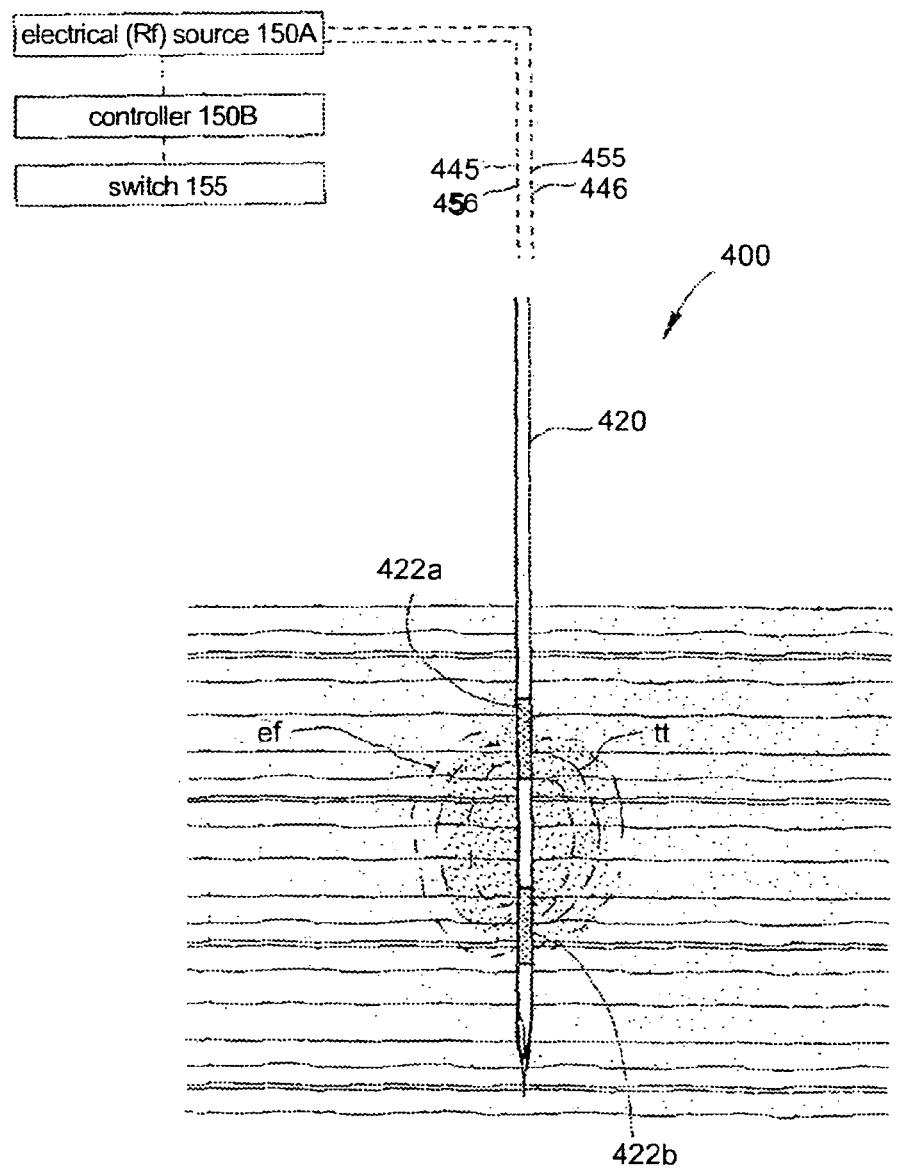
FIG. 15A is a view of another embodiment of Type "C" probe having a linear configuration that carries spaced apart energy delivery surfaces to provide bi-polar modes of operation.
Figure 15B:
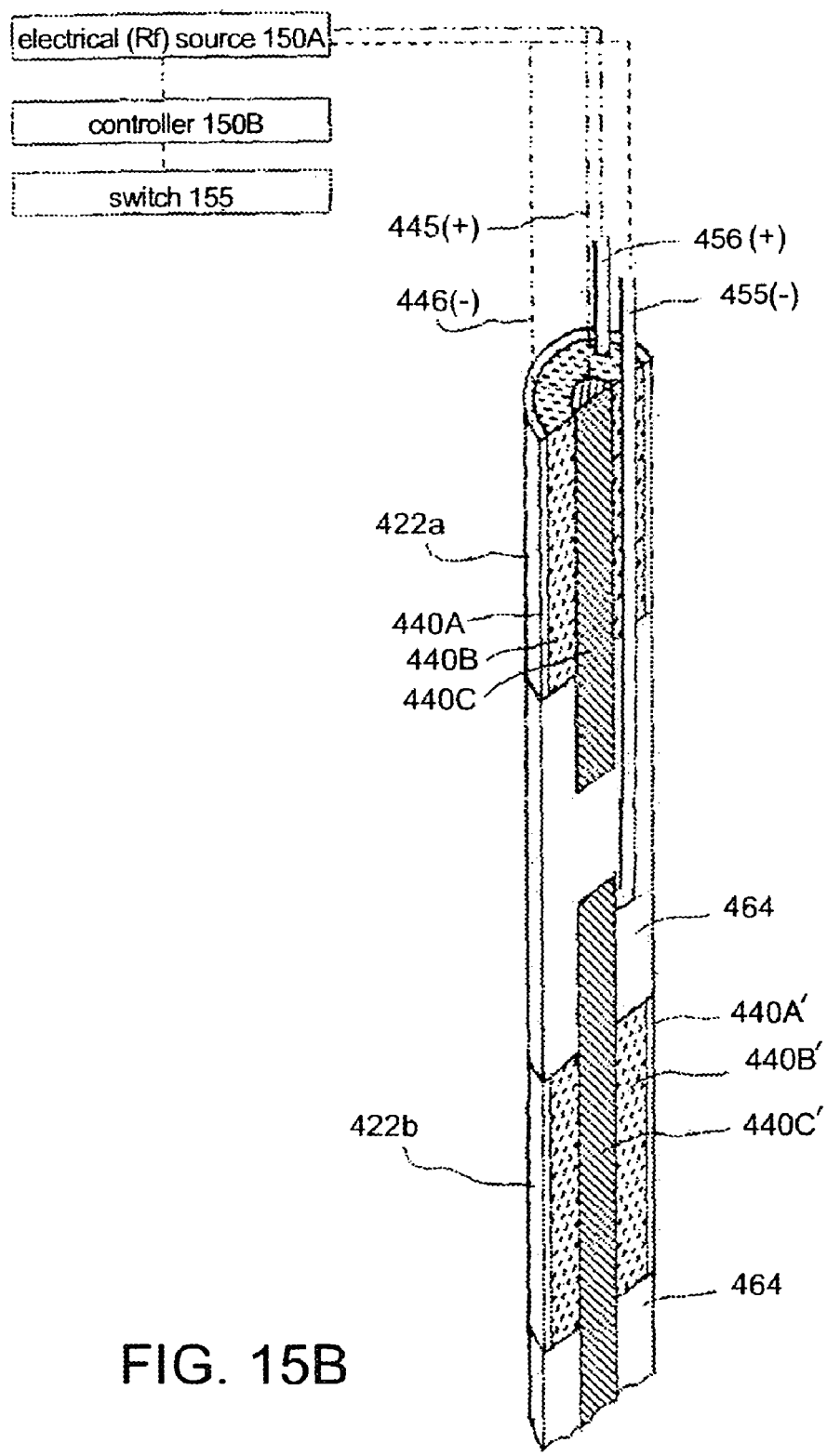
FIG. 15B is a cut-away view of the probe of FIGS. 15A illustrating the components of the plurality of independent energy delivery components and connection to an Rf source.

4. Type "C" probe for tumor ablation. Type "C" probes corresponding to the invention are illustrated in FIGS. 14, 15A & 15B that are adapted for energy delivery to tissue, again described in the treatment of a targeted benign or malignant tumor. FIG. 14 illustrates a Type "C" probe 300 in a sectional view of its working end only that can apply energy to tissue in a manner similar to the Types "A" and "B" embodiments described above. Each energy delivery member 320A–320B defines a surface engagement layer portion 340A, a medial conductive portion 340B of a PTC material and a core conductive portion 340C. In the previously described embodiment of FIG. 8, the multiple energy delivery members 220A–220B operated simultaneously in the same polarity with respect to Rf source 150A and the electrical return. In contrast, the probe 300 of FIG. 14 has two energy delivery members 320A–320B that superficially appear to be identical to the probe of FIG. 8. However, the probe 300 of FIG. 14 operates in a bi-polar fashion so that an Rf energy density is created between the engagement planes 325A–325B of the members 320A–320B by Rf energy flow directly therebetween. In other words, the engagement planes 325A–325B of the members at any point in time would have opposing polarities, as provided by the Rf source 150A and controller 150B. For purposes of explanation, the components of the working end and the electrical leads are indicated with positive (+) and negative (−) polarities which correspond to such polarities a particular point in time during energy delivery. In other respects, the energy delivery members 320A–320B of FIG. 14 are adapted to function as described above to modulate energy application to the targeted tissue tt as the thermally sensitive medial layers 340B of each energy delivery member hovers about its selected switching range. It should be appreciated that the exposed conductive surface portions 340A–340B can be recessed in the engagement planes 325A–325B, or partly covered with an insulator elements to prevent the contact (and shorting) between the surfaces if the needle member deflect and inadvertently contact on another.

FIGS. 15A–15B illustrate another embodiment of Type "C" probe 400 in which an elongate length of a single energy delivery member 420 carry at least two spaced apart sections that comprise conductive engagement planes (e.g., 422a–422b) that are independently coupled to Rf source 150A and controller 150B to function with opposing polarities. In this sense, the invention operates somewhat like the bi-polar arrangement of FIG. 14. As can be seen in FIG. 15A, the exemplary probe 400 defines two independent conductive surface engagement portions 422a–422b, but any number of independent active engagement portions are possible. FIG. 15B illustrates a sectional view of the member 420 with one engagement surface 422a having a conductive engagement portion 440A in contact with the medial PTC layer 440B as described previously. The core conductive electrode portion 440C is coupled by insulated lead 445 to Rf source 150A and controller 150B. The assembly defines a particular polarity at a point in time which, for purposes of explanation is represented by positive (+) and negative (−) polarities in FIG. 15B with the engagement surface portion 440A coupled by lead 446 to the Rf source 150A. The second conductive surface engagement portions 422b has its conductive surface engagement portion 440A' adjacent to medial PTC layer indicated at 440B' which in turn is coupled to core conductive portion 440C'. The core electrode 440C' is coupled by insulated lead 455 to Rf source 150A and controller 50B. The engagement surface portion 440A' coupled by lead 456 to Rf source 150A (connection not visible). The portions of the member 420 not comprising an engagement surface are part of an insulative body portion indicated at 464.

Referring back to FIG. 15A, the effect of using the probe 400 is illustrated wherein lines of an electric field ef are indicated in tissue as current flow can be generally directed between the opposing polarities of the spaced apart engagement surfaces. A probe of this type can be used to apply energy to a precise area. A plurality of probes of this type could be used for penetration into or about a targeted tissue. The probe 400, or plurality thereof, can also cooperate with a ground pad (not shown).

Figure 16A:
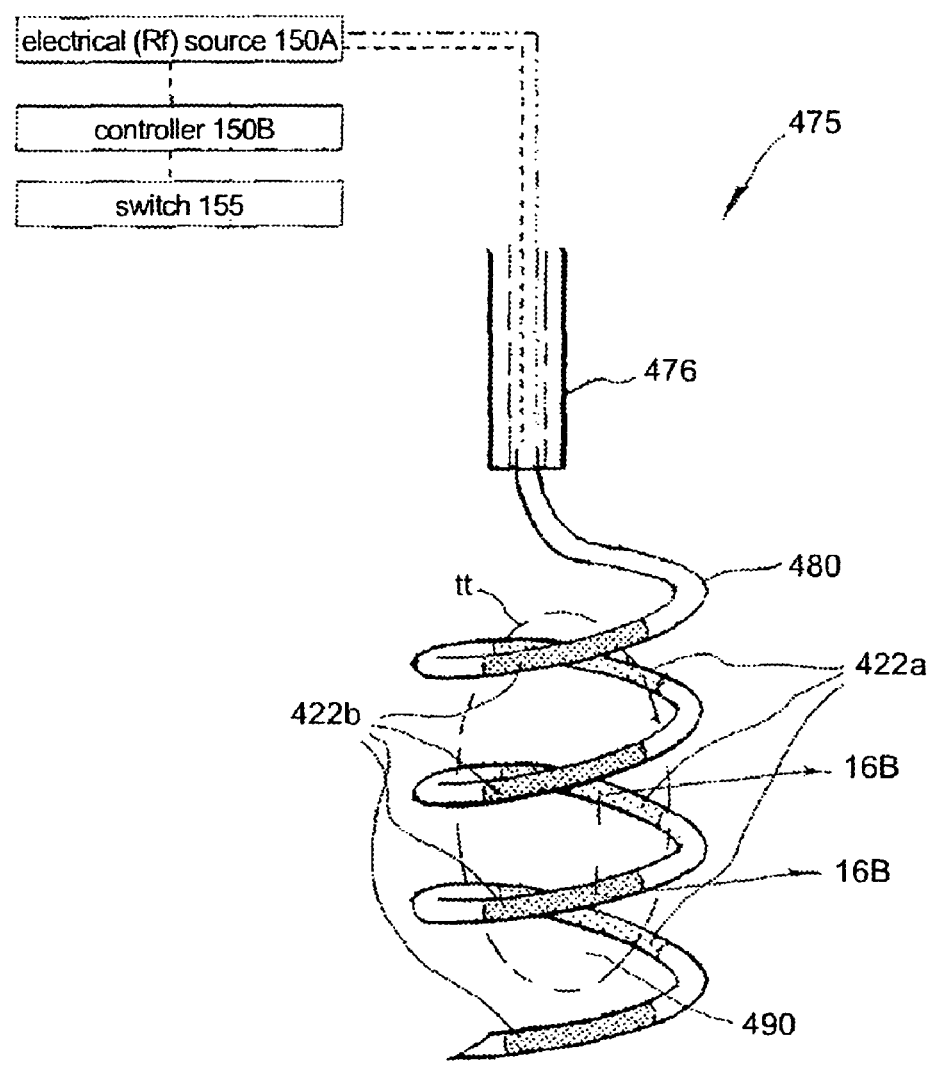
FIG. 16A is a view of another embodiment of Type "C" probe having a helical configuration that carries spaced apart energy delivery surfaces on opposing sides of a helical member to provide bi-polar modes of operation.
Figure 16B:
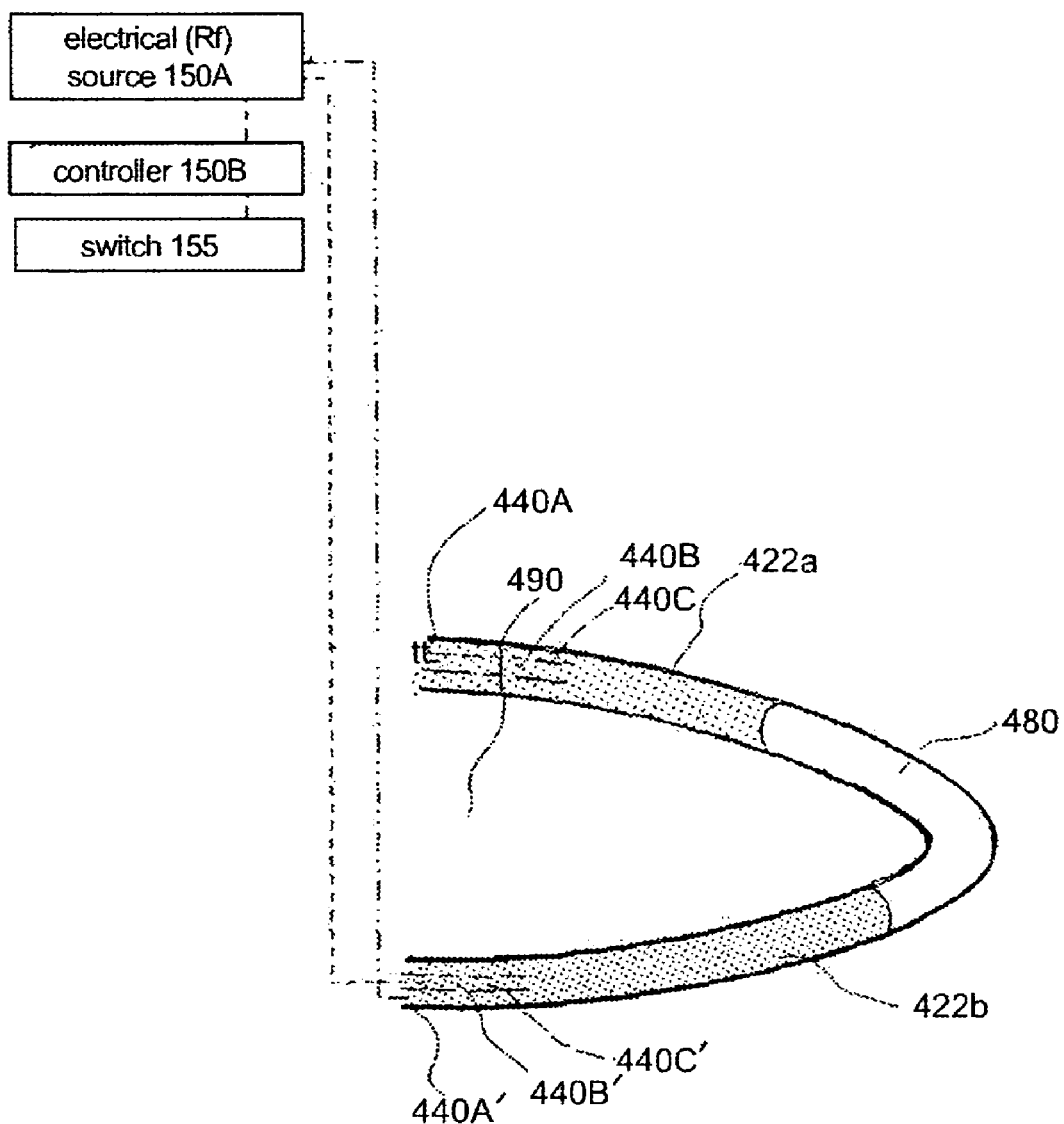
FIG. 16B is an enlarged view of a portion of the probe of FIG. 16A illustrating the electrical field and localized energy density that can be created across the center portion of a helical member.

FIGS. 16A–16B illustrate another preferred embodiment of probe 475 that operates exactly as described above in the probe of FIGS. 15A–15B. The only difference is that introducer 476 slidably carries an energy delivery member 480 that has a helical configuration when deployed from the introducer to thereafter be disposed in a helical manner about a targeted tissue tt (phantom view). In this embodiment, the paired engagement portions 422a–422b are again independent as described in the probe of FIG. 15A. Each engagement surface 422a and 422b has the same a conductive surface portion (440A or 440A') in contact with the medial PTC layer (440B or 440B') and core conductor (440C or 440C') as illustrates in the previous embodiment (see FIG. 15B). As can be seen in FIG. 16A, the segmented engagement surfaces can be carried on opposing sides of the energy delivery member 480 when in its deployed-expanded position.

FIG. 16B shows an enlarged view of a portion of the helical energy delivery member 480 to further depict that manner of operation. By providing a helical means of deployment, the opposing energy delivery surfaces engagement surface 422a and 422b can cause an electrical field and Rf energy density across the center 490 of the helix to focus the application of energy to tissue that is circumscribed by the energy delivery member 480. The energy delivery member 480 of FIG. 16B thus is adapted to function as described previously to modulate energy application to the targeted tissue tt as each thermally sensitive medial layer of the working end hovers about its selected switching range.

Figure 17:
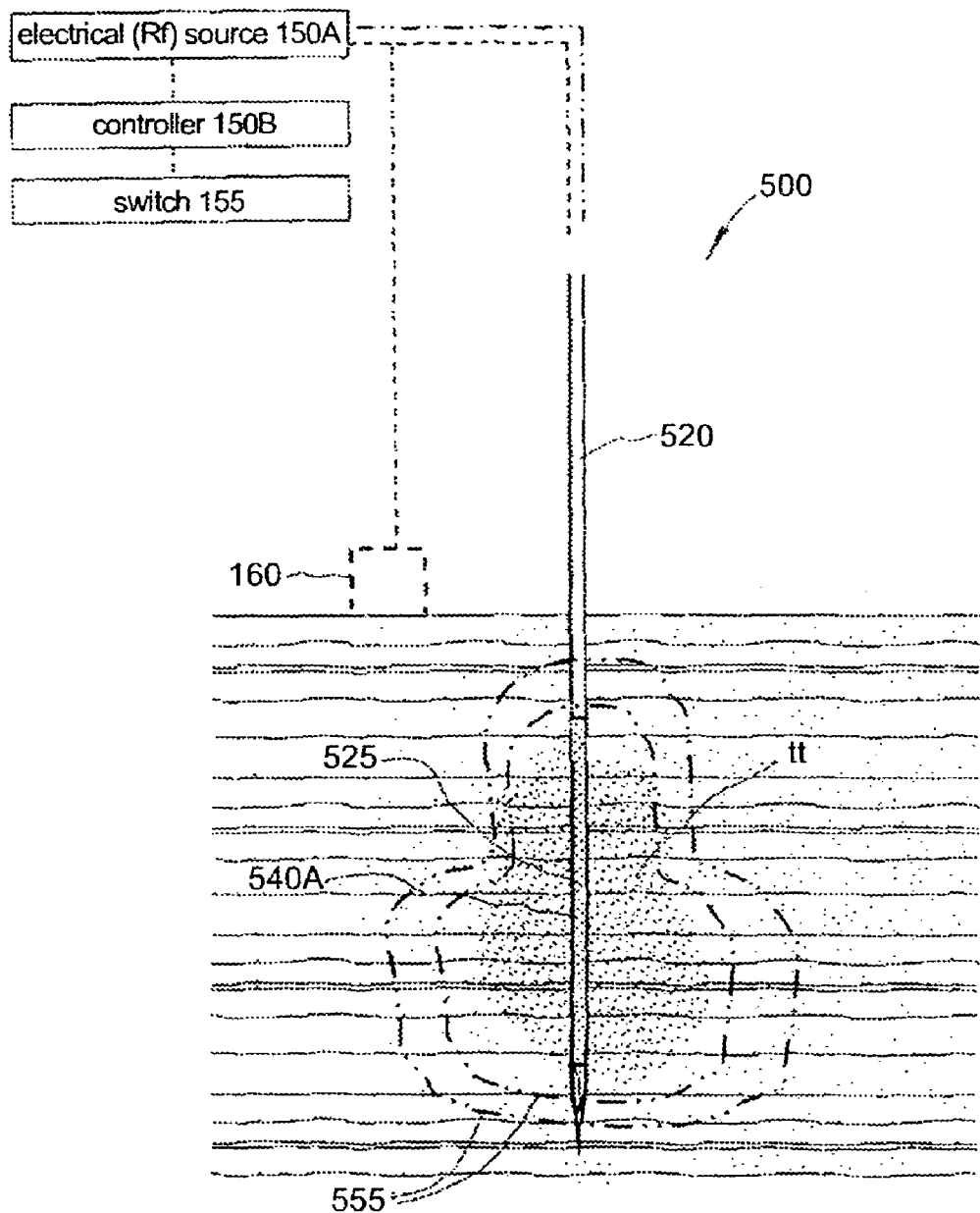
FIG. 17 is a view of the distal end of a Type "D" probe that carries first and second PTC components to provide an alternative form of energy application to tissue.
Figure 18:
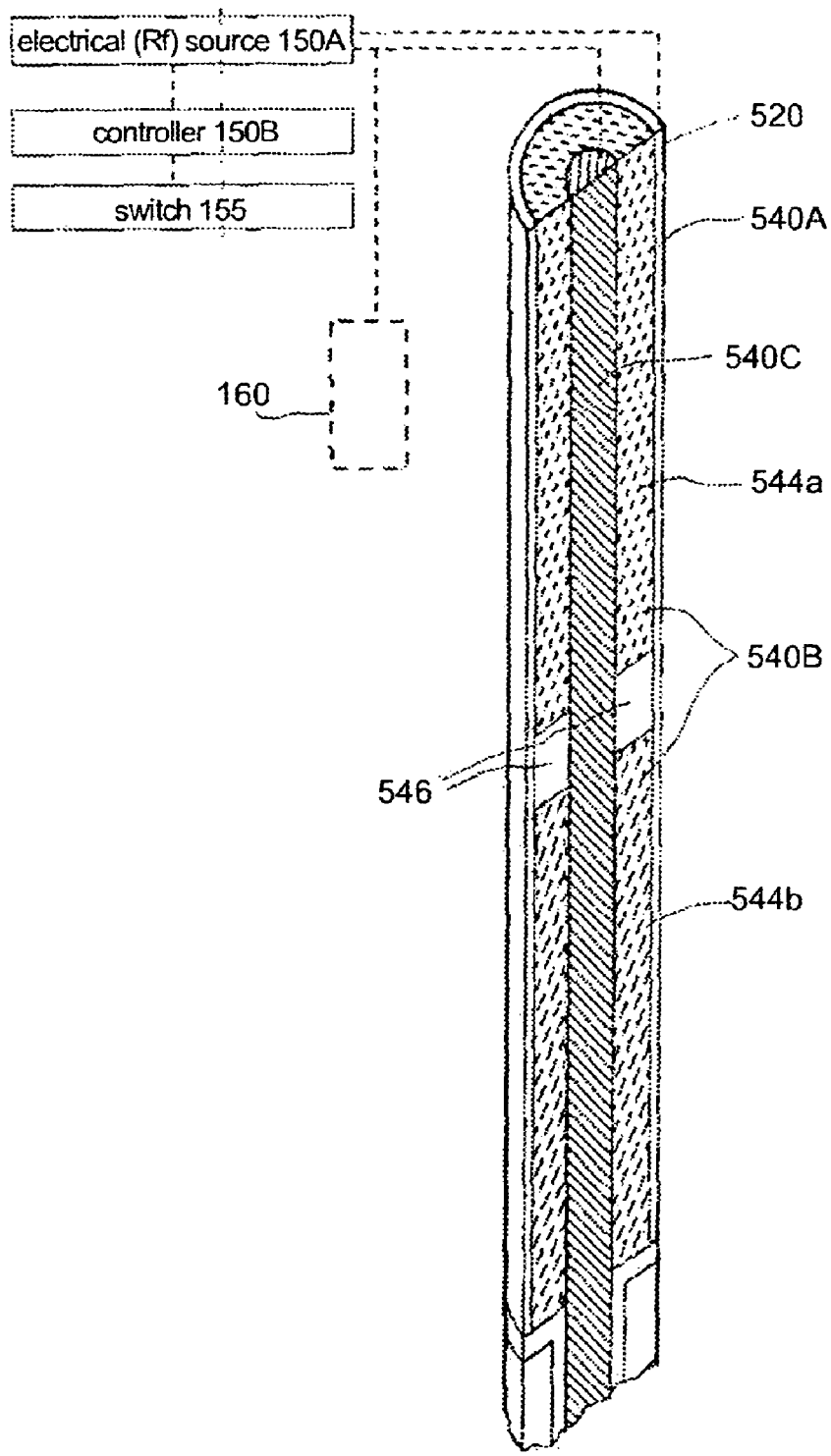
FIG. 18 is a sectional view of the Type "D" probe of FIG. 17.

5. Type "D" probe for tumor ablation. An exemplary working end of a Type "D" probe 500 of the invention is illustrated in FIGS. 17 and 18 that again is adapted for energy delivery to a targeted tumor tissue. The energy delivery member 520 defines an engagement plane 525 that differs from the Types "A" and "B" embodiments in its ability to provide a selected energy delivery profile across the dimensions of the engagement plane 525. The working end again comprises a conductive surface engagement plane or portion 540A that overlies the medial conductive portion 540B that us fabricated of a PTC-type material (see FIG. 18). The surface conductive 540A portion in this exemplary embodiment is indicated as a thin metallic layer. The variable conductive medial portion 540B can be a rigid ceramic material of the Type "A" embodiment or a flexible silicone-based material as described in a Type "B" embodiment. The probe again has a core conductive portion (electrode) 540C that is coupled to the variable conductive medial portion 540B. The core conductive electrode 540C again is coupled to electrical source 150A and controller 150B, as described previously. Of particular interest, referring to FIG. 18, the variable conductive medial portion 540B comprises at least two spaced apart portions 544a and 544b that each are of a different PTC-type composition with each having a different selected switching range. FIG. 18 illustrates an insulative material 546 of any suitable dimension positioned between the two medial conductive portions 544a and 544b.

As an example, assume that the probe of FIG. 18 is fabricated with a proximal variable conductive portion 544a that has a switching range around 70° C. The more distal variable conductive portion 544b has a switching range around 85° C. In operation, it can be understood how the application of active Rf energy to targeted tissue tt can create "shaped" isotherms 555 around a tumor. FIG. 18 is a graphic representation of the type of energy application and thermal effects that can be achieved. It should be appreciated that the scope of the invention includes any working end fabrication that utilizes a plurality of PTC-type compositions for shaping energy application. The different conductive portions 544a–544n (where n represents the plurality of PTC conductors) of an exemplary engagement plane 525 can extend along axial portions of a needle, can extend in radial portion about a needle, can comprise different axial or concentric portions of an engagement surface of a jaw or other tissue contacting member as shown in FIGS. 12–13.

Figure 19:
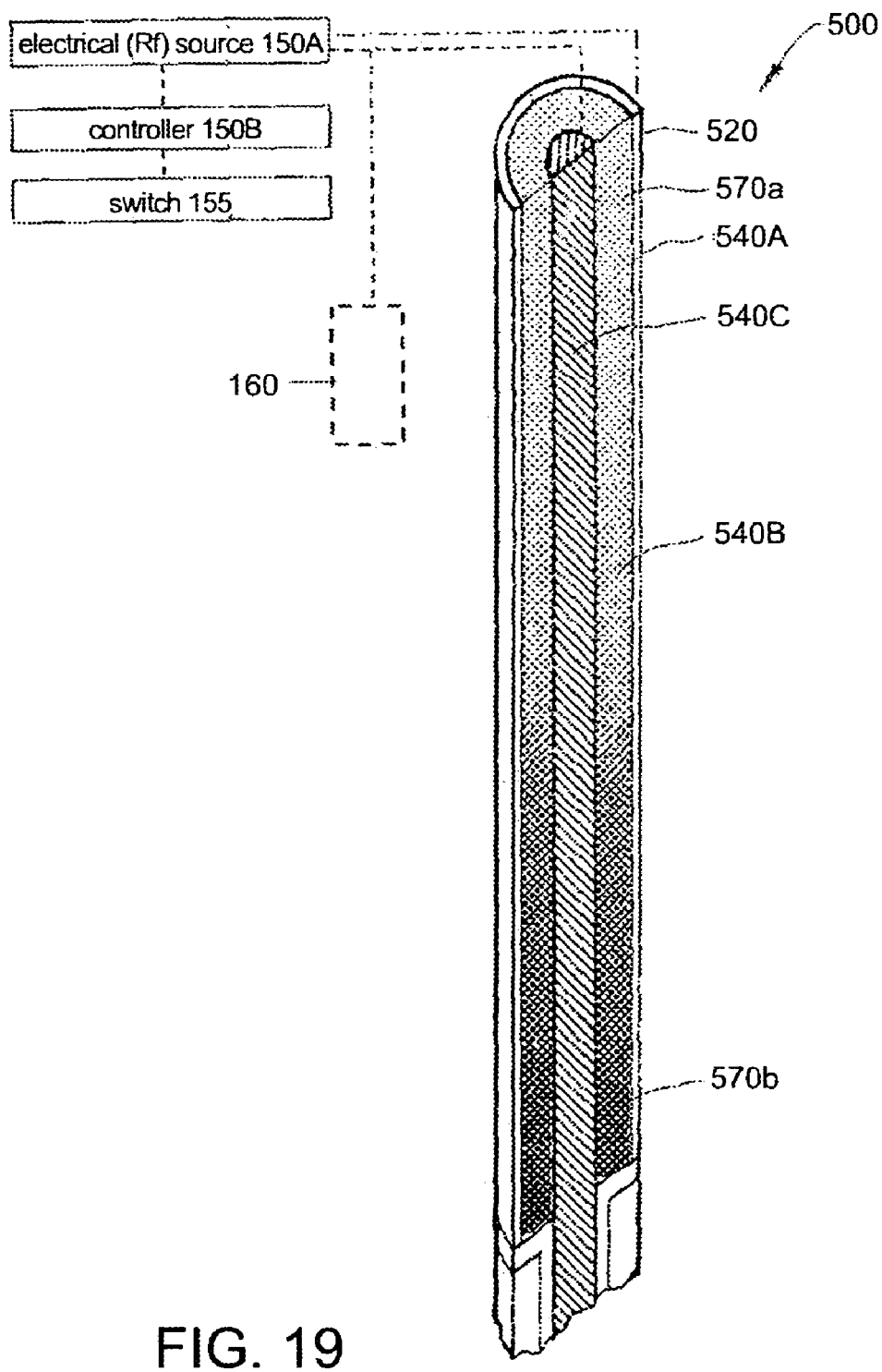
FIG. 19 is a sectional view of an alternative Type "D" probe with a gradient type of PTC component to provide form of energy application to tissue.

FIG. 19 illustrates another embodiment of Type "D" working end that is very similar to the embodiment of FIG. 18. In FIG. 19, the conductive engagement plane or portion 540A and core electrode 540C are identical to the probe of FIG. 18. The variable conductive medial portion indicated at 540B differs in that it comprises a substrate composition that has a first end 570a having a first selected switching range with a PTC gradient that extends over the dimension of the medial portion 540B to a second end 570b that has a second selected switching range. It is possible to manufacture either the rigid ceramic PTC type materials of the Type "A"

embodiment or the flexible silicone-based materials of the Type "B" embodiment with such a temperature-resistance gradient.

Figure 20:
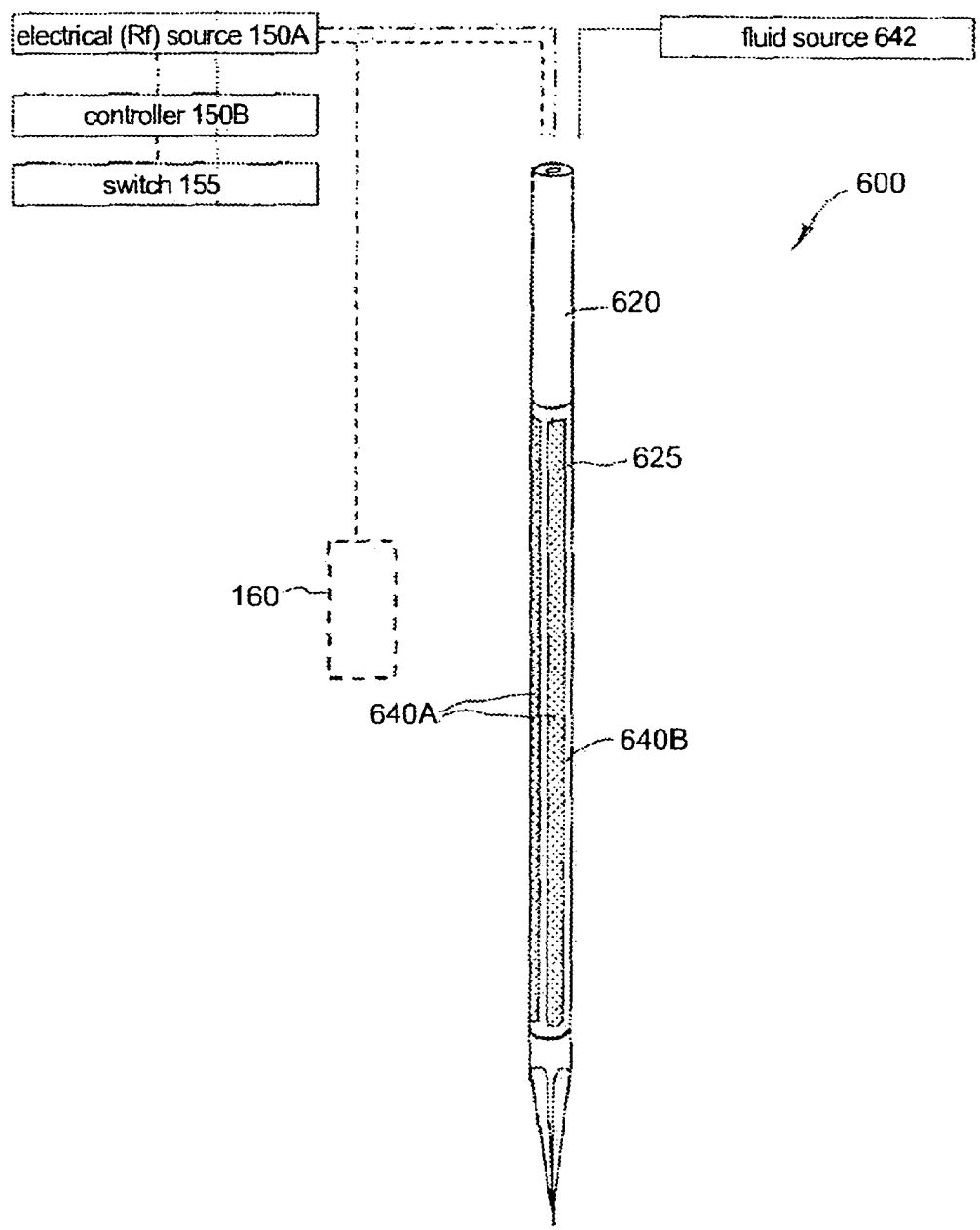
FIG. 20 is a plan view of the distal end of a Type "E" probe that has an open cell compressible PTC component for providing fluid flow to the engagement plane.
Figure 21:
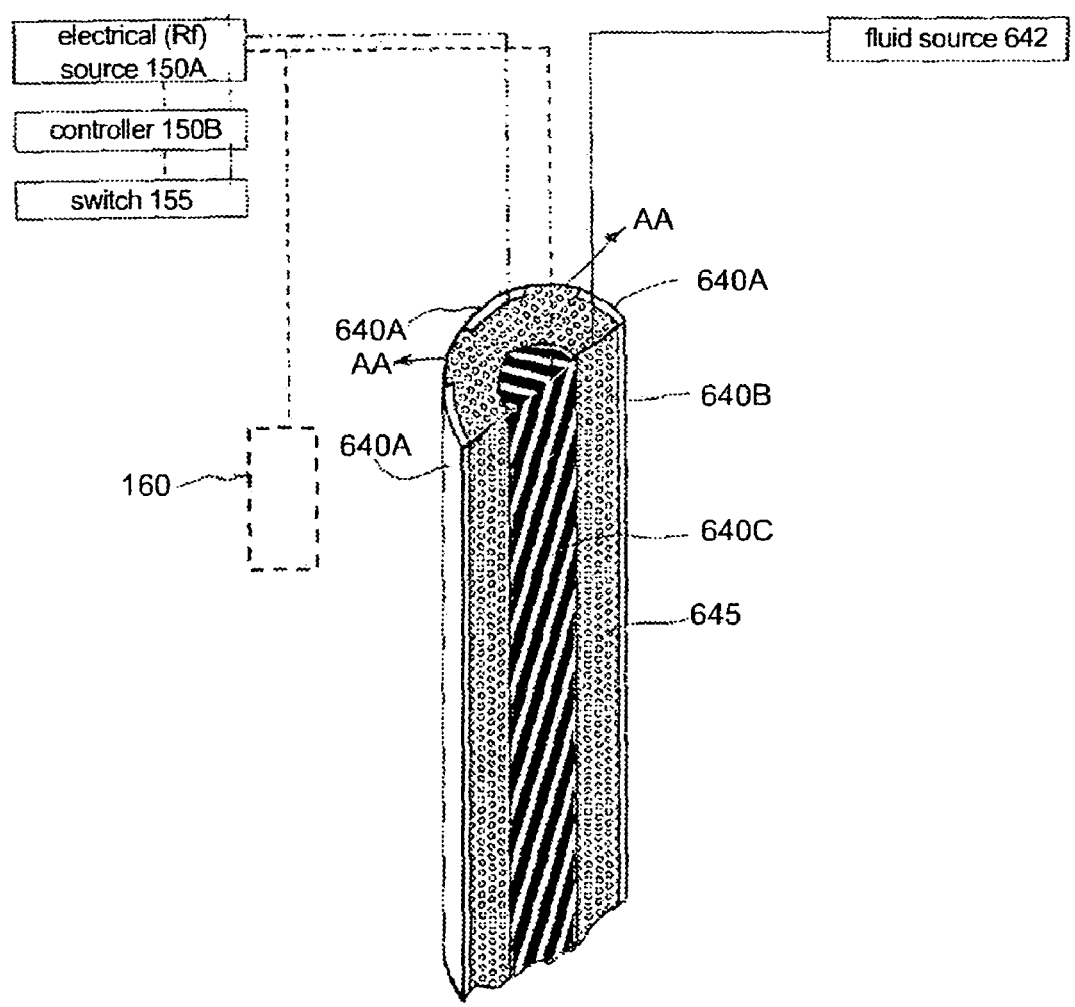
FIG. 21 is a sectional view of the Type "E" probe of FIG. 20.

6. Type "E" probe for energy delivery to tissue. FIGS. 20 and 21 illustrate the working end of a Type "E" probe 600 corresponding to the invention. The probe again is adapted for energy delivery to a targeted tumor tissue, this time utilizing another embodiment of the flexible-compressive PTC-type material of the Type "B" embodiment described previously. In FIG. 20, it can be seen that energy delivery member 620 defines an engagement plane 625 that extends along an axial portion of the probe body. The conductive surface engagement portion 640A comprises a plurality of elongate conductive elements that expose therebetween portions of the compressible medial conductive portion 640B. The medial conductive portion 640B is silicone-based PTC type material as described above in relation to FIGS. 8–13. (Alternatively, the surface could be a thin microporous metallic coating). The probe has a core conductive portion (electrode) 640C that is coupled to electrical source 150A and controller 150B, as described previously. In this embodiment, referring to FIG. 21, the system is adapted to deliver saline flow from fluid source 642 directly through an open cell structure of the silicon-based medial conductive layer. Such an open cell silicone can be provided adding foaming agents to the silicone during its forming into the shape required for any particular working end. The silicone has a conductive material added to matrix as described above, such as carbon.

In use, referring to FIG. 21, the system can apply saline solution through pores 645 in the medial conductive portion 640B that are exposed at the exterior of the probe (see arrows AA) proximate to the plurality of conductive surface engagement portions indicated at 640A. As described above in relation to FIG. 10B, one method of the invention provides for the infusion of saline during an interval of energy application to tissue to enhance both active Rf heating and conductive heating as the system maintains tissue temperature at the selected switching range of the medial conductive portion 640B. In another aspect of the invention, the compressibility of the silicone-based medial conductive portion 640B can alter the volume and flow of saline within the open cell silicone medial conductive portion 640B. Since the saline is conductive, it functions as a conductor within the cell voids of the medial conductive portion 640B, and plays the exact role as the carbon doping does within the walls of cells that make up the silicone. Thus, the extent of expansion or compression of the silicone medial conductive portion 640B alters its resistivity, when the conductive doping of the material is somewhat static. Thus, this effect can be used to design into the working end certain PTC characteristics of to cause the working end to perform in an optimal manner.

Figure 22:
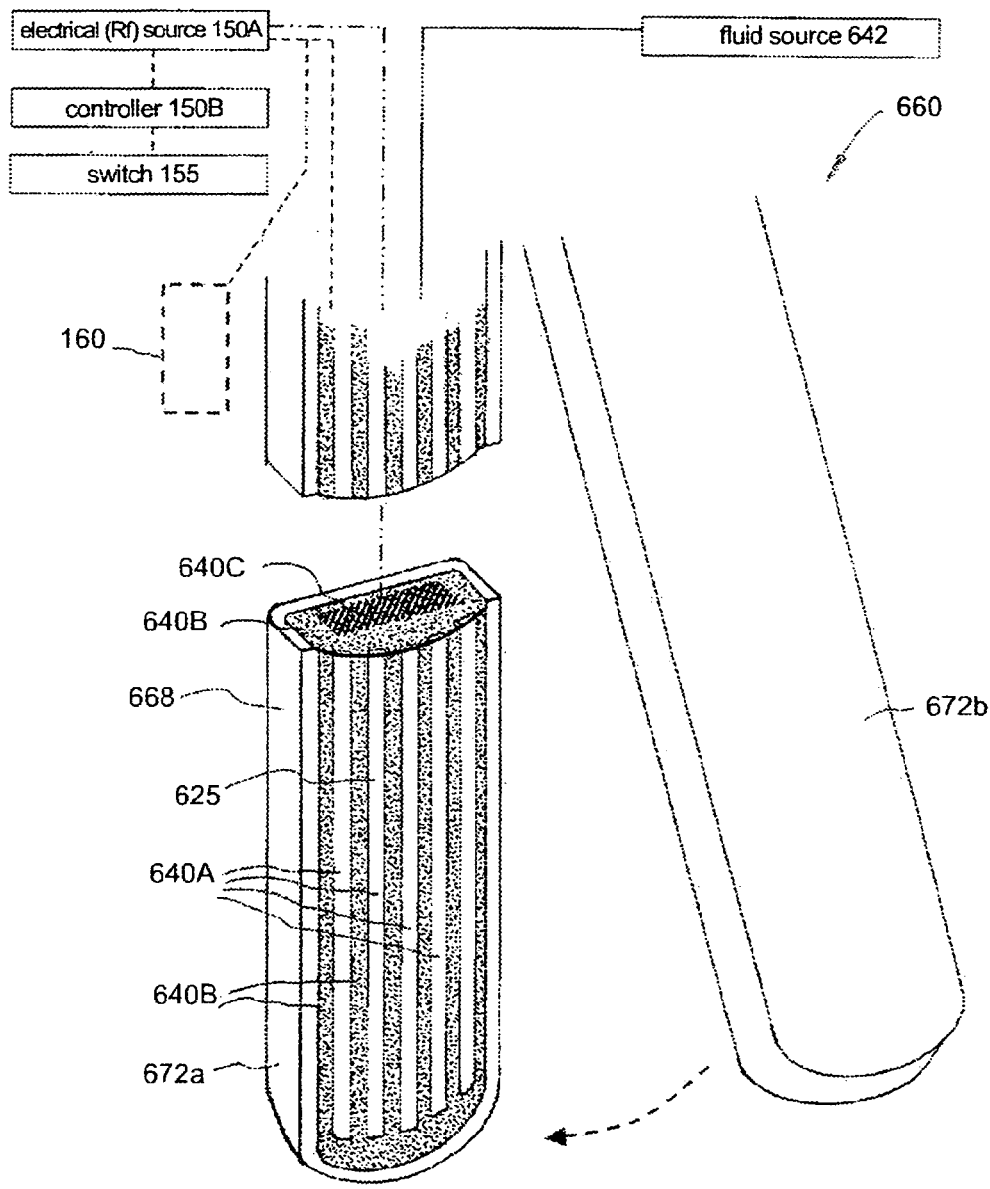
FIG. 22 is a cut-away view of an alternative Type "E" probe with an openable-closeable jaw structure.

FIG. 22 illustrates another embodiment of probe working end 660 that utilizes the same principles in a tissue-clamping arrangement. The working end again defines an engagement plane 625 that has a conductive surface engagement portion 640A comprising a plurality of axial conductive strips. Also exposed in the engagement plane are portions of the compressible medial conductive portion 640B. Again, the medial conductive portion 640B is silicone-based PTC-type material as described above in relation to FIGS. 8–13, and 20–21. (Alternatively, the surface 625 can be a thin microporous metallic coating). FIG. 22 shows a core conductive portion (electrode) 640C covered by the medial conductive portion 640B. The core conductive portion 640C is coupled to electrical source 150A and controller 150B, as described previously. The embodiment of FIG. 22 has the medial conductive portion 640B coupled to a lumen (not shown) that is adapted to deliver saline flow from fluid source 642.

Figures 23A, 23B:
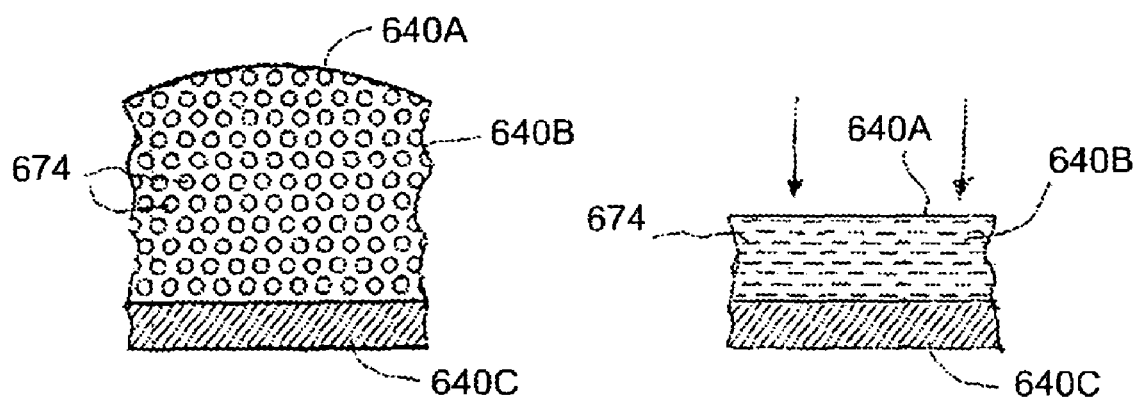
FIG. 23A is a schematic view of an open cell compressible PTC component similar to that of FIG. 22 in a non-compressed condition.
FIG. 23B is a schematic view of the open cell compressible PTC component of FIG. 23A in a compressed condition.

The probe working end 660 has a first jaw portion 672a that carries the above described functional components of the invention attached to any suitable jaw body indicated at 668. The jaw body 668 is of an insulated material or a metal with a non-conductive coating. The second jaw portion 672b is moveable about a pivot (not shown) to close against the first jaw 672a as indicated by the arrow in FIG. 22. The tissue-engaging surface of the second jaw portion preferably is a non-conductive material. Any suitable jaw opening-closing mechanism known in the art can be used with either one both jaws being actuatable from an instrument handle. It can be understood that by closing the jaws to clamp a targeted tissue volume therebetween, the silicone-based medial conductive portion 640B will compress inwardly, depending on the density selected. If the open cells of the medial conductive portion 640B are collapsed to any substantial extent as the jaws are compressed, the flow of saline through medial conductive portion 640B will be restricted thus altering the temperature coefficient of resistance of the medial conductive portion 640B. FIGS. 23A–23B illustrate schematically the potential for fluid flow through the medial conductive portion 640B, with FIG. 23A indicating that open cells 674 allow fluid flow therethrough. It can be easily understood from FIG. 23B that a compression of medial conductive portion 640B can collapse the cells 674 which in turn will restrict fluid flow. Thus, the system can be designed with (i) selected conductive doping of medial conductive portion 640B and (ii) selected conductivity of the saline solution to optimize the temperature coefficient of the material under different compressed and uncompressed conditions for any particular thermally-mediated therapy. The medial conductive portion 640B can be designed to be a positive or negative temperature coefficient material (defined above) as the material expands to a repose shape after being compressed. For example, one thermal treatment using the jaws of FIG. 22 can be to seal or coagulate engaged tissue. The resilient engagement surface 625 can naturally expand to remain in substantial contact with the tissue surface as the tissue is sealed and dehydrates and shrinks. At the same time, the cell structure of the medial conductive portion 640B would tend to open to thereby increase fluid flow the engagement plane, which would be desirable to maintain active and passive conductive heating of the tissue. Also at the same time, the selected temperature coefficient of the medial conductive portion 640B in combination with the saline volume therein can insure that active Rf heating is modulated as exactly described in the Types "A" and "B" embodiments above with any selected switching range.

Figure 24:
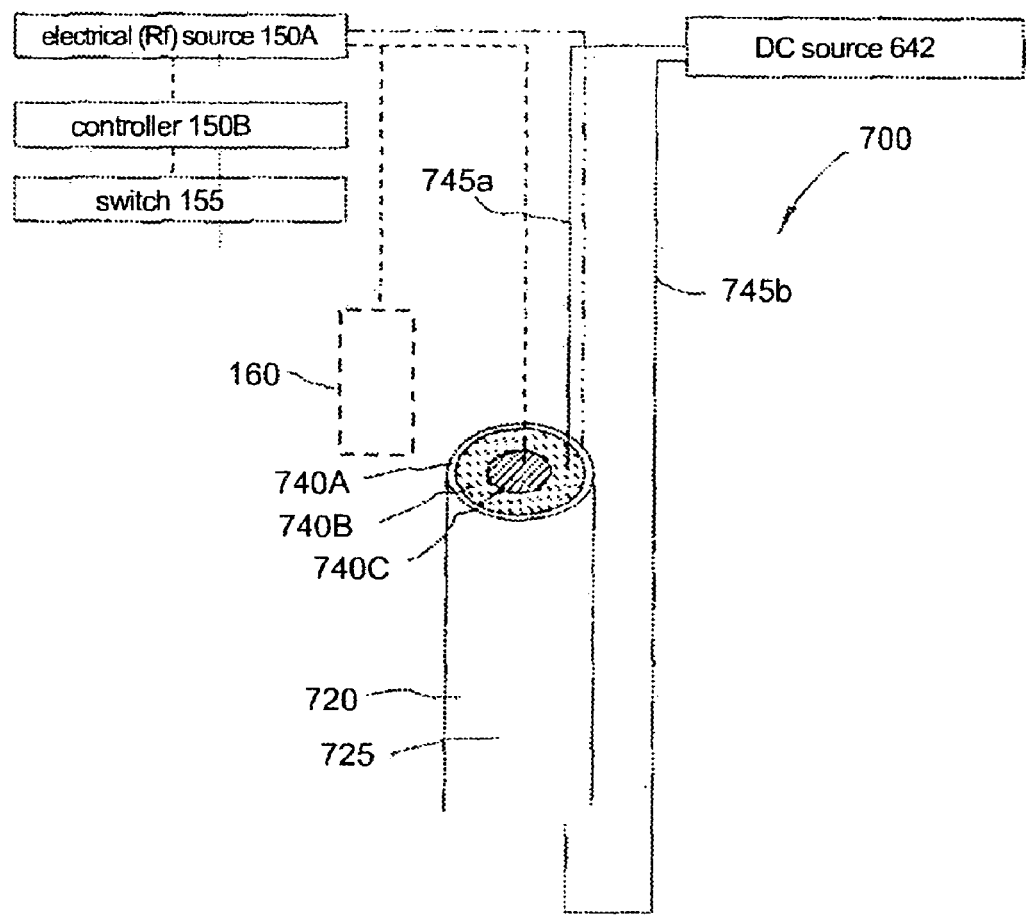
FIG. 24 is a cut-away view of the distal end of a Type "F" probe that has a DC source coupled to the medial conductive portion.

7. Type "F" probe for energy delivery to tissue. FIG. 24 illustrates alternative a Type "F" probes 700 that correspond to the invention. The working end of the probe differs from the Type "A" embodiment, for example, in that an additional control mechanism is added to the system. FIG. 24 shows a needle-type probe member 720 that defines engagement plane 725 extending about its distal surface. The conductive surface engagement portion 740A and medial conductive portion 740B are as described previously. The medial conductive portion 740B again is a PTC-type material adjacent the core conductive (electrode) 740C. In this embodiment, referring to FIG. 24, the system has independent (insulated) electrical leads 745a and 745b extending through the probe that are coupled to medial conductive portion 740B. The leads are connected to a DC source 750 and controller 150B.

The purpose of the DC delivery application mechanism is to provide independent control means for modulating the temperature of medial conductive portion 740B. The DC system can be used to instantly alter the temperature of a PTC or NTC material, for example, to terminate Rf energy application or for other similar control purposes. Another purpose of such a DC system would be to shift the switching range to a higher or lower range. Another embodiment (not shown) can use photonic energy application means to alter the resistance of an optically sensitive medial conductive layer 740B for similar purposes.

Figure 25:
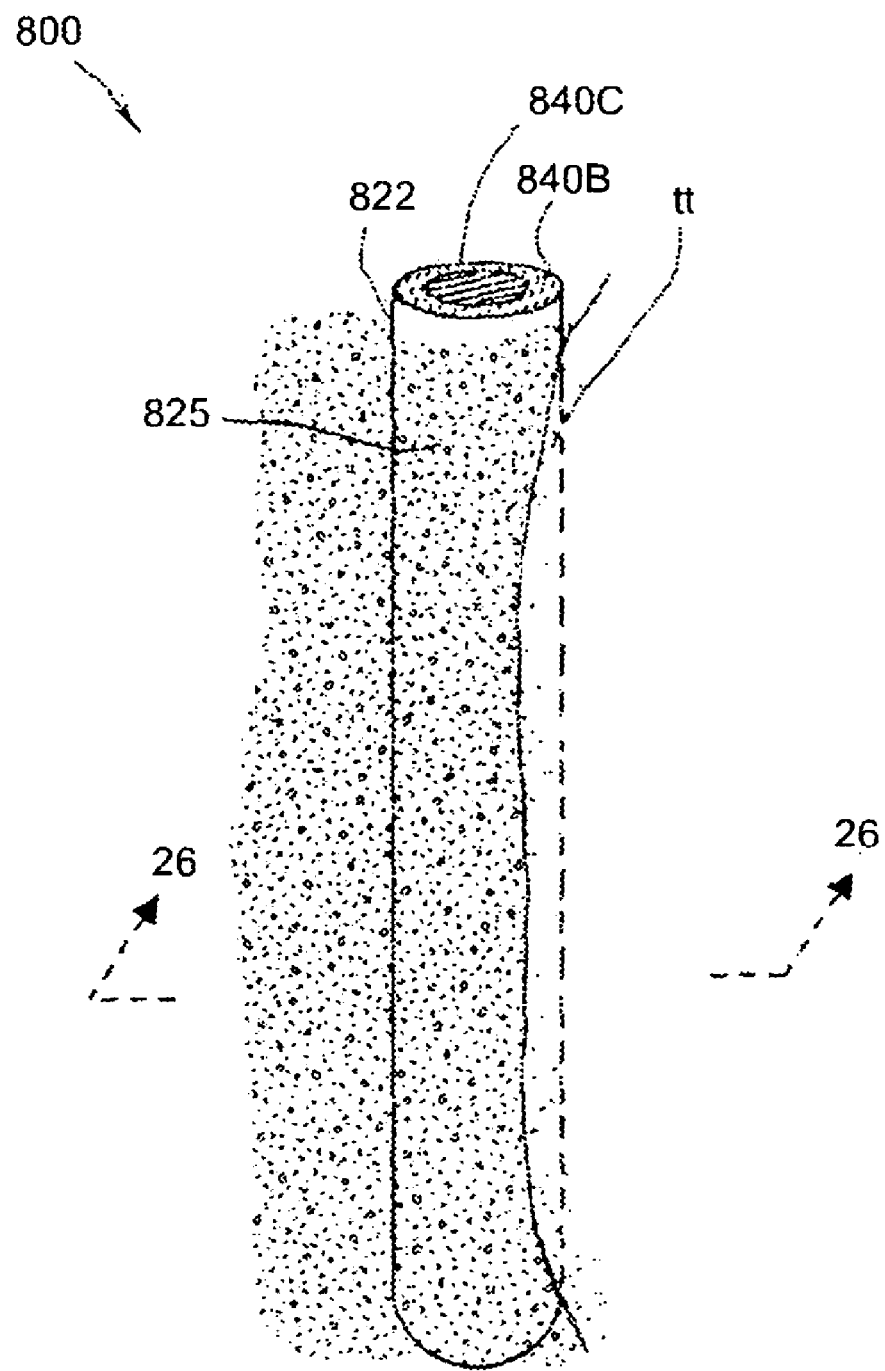
FIG. 25 is a view of the working end of a Type "G" probe corresponding to the invention that comprises a distal end of a catheter carrying a negative temperature coefficient material.
Figure 26:
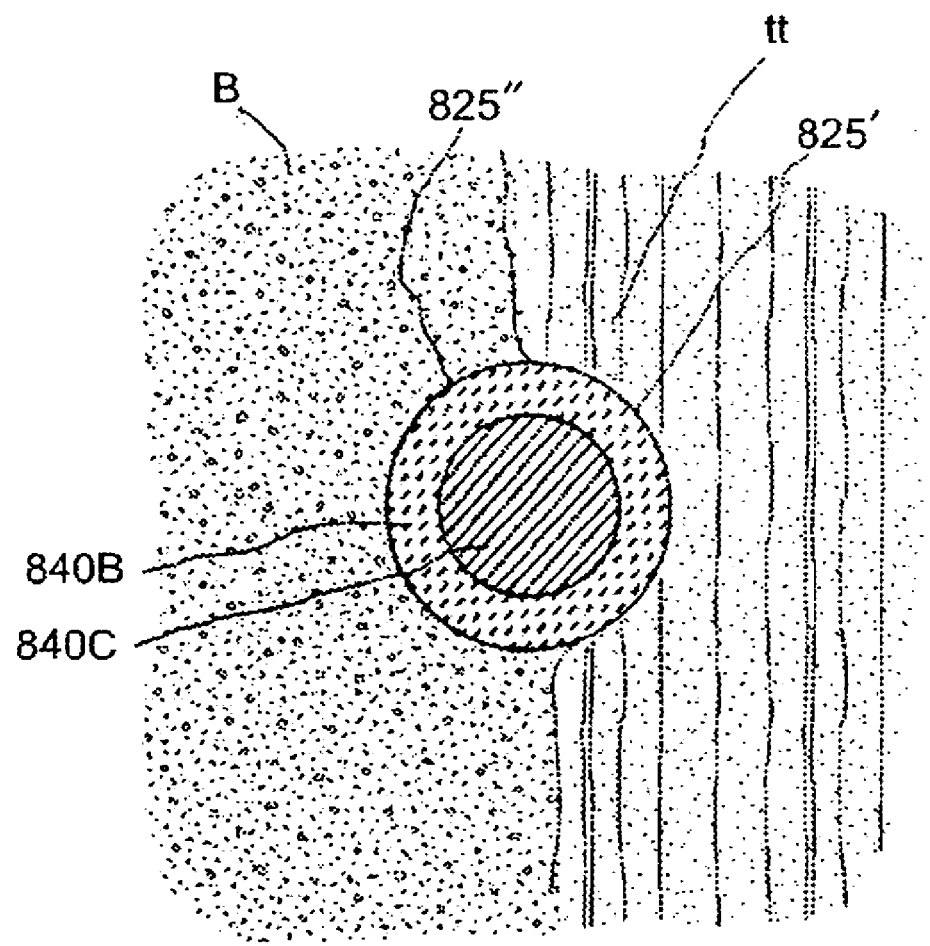
FIG. 26 is a sectional view of the Type "G" probe of FIG. 25 showing its use in a fluid environment.

6. Type "G" probe for energy delivery to tissue. FIGS. 25 and 26 illustrate the working end of a Type "G" probe 800 corresponding to the invention. The probe again is adapted for controlled energy delivery to tissue utilizing a variably resistive matrix that is dependent on its temperature—but this embodiment comprises the working end 822 of a probe (e.g., a catheter) that is adapted for introduction into a lumen, space, or cavity in or about the patient's body. The working end defines an engagement plane 825 that extends around the circumference of the probe. The embodiment of FIG. 25 has a conductive surface portion 840A that overlies the variably resistive matrix indicated at 840B. The core electrode 840C can be a flexible conductive tube or wire, or a flexible polymer with a metallic coating that serves as an electrode. While the probe 800 is shown as being flexible for endoluminal navigation, the probe shaft also can be rigid for introducing into a joint capsule or similar body space.

The Type "G" probe is adapted for operation in an environment in which the targeted tissue tt is exposed to fluid environment, wherein the term fluid is defined as any flowable media such as a liquid or a gas. The variably resistive matrix 840B can be a positive temperature coefficient material (PTC) or a negative temperature coefficient material (NTC), depending on the operating environment. Either a PTC or NTC material has the characteristic that its temperature—and therefore its selected switching range—can extend over only a highly localized portion of the working end. Thus, in operation, one portion of the variably resistive matrix 840B can be substantially resistive while another portion can be substantially conductive.

As one example of such a Type "G" probe, FIG. 25 depicts the working end 822 in a patient's heart in a catheter ablation treatment to correct an arrhythmia. Supraventricular tachycardia (SVT) is a general term describing any rapid heart rate originating above the ventricles, or lower chambers of the heart. SVT is an arrhythmia, or abnormal heart rhythm, that includes atrial fibrillation, AV nodal re-entrant tachycardia, and Wolff-Parkinson-White syndrome. SVT can occur for a number of reasons, including abnormalities of the heart's electrical conduction system. Rf catheter ablation can correct an arrhythmia by creating lesions, for example, in the atrial wall to eliminate alternate conductive pathways in the heart that interfere with the normal conduction pathways. The objectives of such an Rf ablation are to create a fill-depth lesion in the targeted wall with as little collateral damage as possible. Further, it is important that such Rf ablation does not char the tissue or coagulate blood which can create embolic material. Such emboli can migrate downstream and cause a stroke or other ischemic event.

FIG. 25 shows the working end 822 in a patient's heart with one side of the engagement plane 825 contacting the targeted tissue tt and the other side exposed to the flow of blood B. It can be understood that the tissue and fluid flow, while both being electrically conductive, will have substantially different impedance characteristics when exposed to electrical potential. Typically, the blood flow about one side of the working end 822 will absorb and subtract heat form the region. In using a prior art Rf working end for catheter ablation, the electrode portion in contact with tissue will deliver energy to the contacted tissue, but at the same time heating blood in contact with the electrode. A typical prior art Rf working end uses thermocouples and feedback circuitry to modulate power as mean for controlling temperature. Since the prior art thermocouples measure temperature of the electrode—not actual tissue temperature—the system's controller cannot determine whether the electrode portion that actually contacts the tissue is at the desired temperature. At best, the thermocouple will signal an approximate temperature that is somewhere between the temperature of the blood and the contacted tissue. It is this uncertain electrode temperature in prior art catheters that can easily result in localized high power densities that create eschar and emboli.

The working end 822 of FIG. 25 is adapted to overcome the problems of prior art Rf catheters by insuring that transient high energy densities cannot occur in the fluid environment. The portion of the engagement plane indicated at 825' can be wedged into substantial contact with the tissue by any suitable means known in the art (e.g., articulating portions, shape-memory materials, balloons, etc.). Another portion of the engagement plane indicated at 825" is exposed to circulating blood. The sectional view of FIG. 26 indicates the use of an NTC variably resistive material 840B. In other words, the NTC material becomes substantially conductive at its selected switching range, for example any selected temperature between about 60 and 900° C. At the switching range, the resistance of the NTC material 840B will drop from a high base resistance to a very low resistance (the opposite of FIG. 7A). In operation, the working end will apply active Rf energy to the targeted tissue tt through engagement plane portion 825' at a lower level until that portion is elevated in temperature to its switching range by contact with the heated tissue. Thereafter, such active energy application will be maintained or enhanced. At the same time, the blood circulation would cool the portion of the engagement plane indicated at 825" that is not in contact with the tissue. Thus, the portion of the NTC material 840B that underlies engagement plane portion 825" will remain at a high base resistivity and substantially prevent the application of energy to the blood By this means, effective application of energy to the targeted tissue can be maintained—while at the same time blood will not be coagulated about the working end. Further, all these objectives can be achieved without relying of thermocouples, feedback circuitry and power controllers.

The NTC matrix 840B can be fabricated of carbon and a zirconium oxide paste, for example, from about 5% to 50% carbon and 95% to 50% zirconium oxide. More preferably, the matrix can be from about 10% to 30% carbon and the balance of zirconium oxide. In one embodiment, the NTC matrix is preferably between about 10% to 12% carbon and 88% to 92% zirconium oxide. It is believed that an elevation of the temperature of the matrix decreases it resistance by slight thermal expansion of the carbon particles that reduces the effective distance between the conductive particles thereby enhancing electrical conduction through the matrix.

The above-described operation of a Type "G" probe in a fluid environment explains the advantages of an NTC matrix to assure active tissue heating when the fluid volume is substantial or dynamic, thus subtracting heat from the region of the working end. A similar probe working end can be used advantageously in a different fluid environment wherein the fluid is not circulating or the fluid is highly conductive. As an example, an orthopedic workspace can have a limited volume of saline therein while performing an arthroscopic procedure. The PTC material in a probe working end similar in form to FIGS. 25–26 will substantially terminate active Rf heating of the fluid as the engagement surface 825" (see FIG. 26) reaches its switching range. At the same time, both active and passive energy application to the targeted tissue will be maintained through engagement surface 825' (see FIG. 26) as described in the Type "A" embodiment above.

Figure 27:
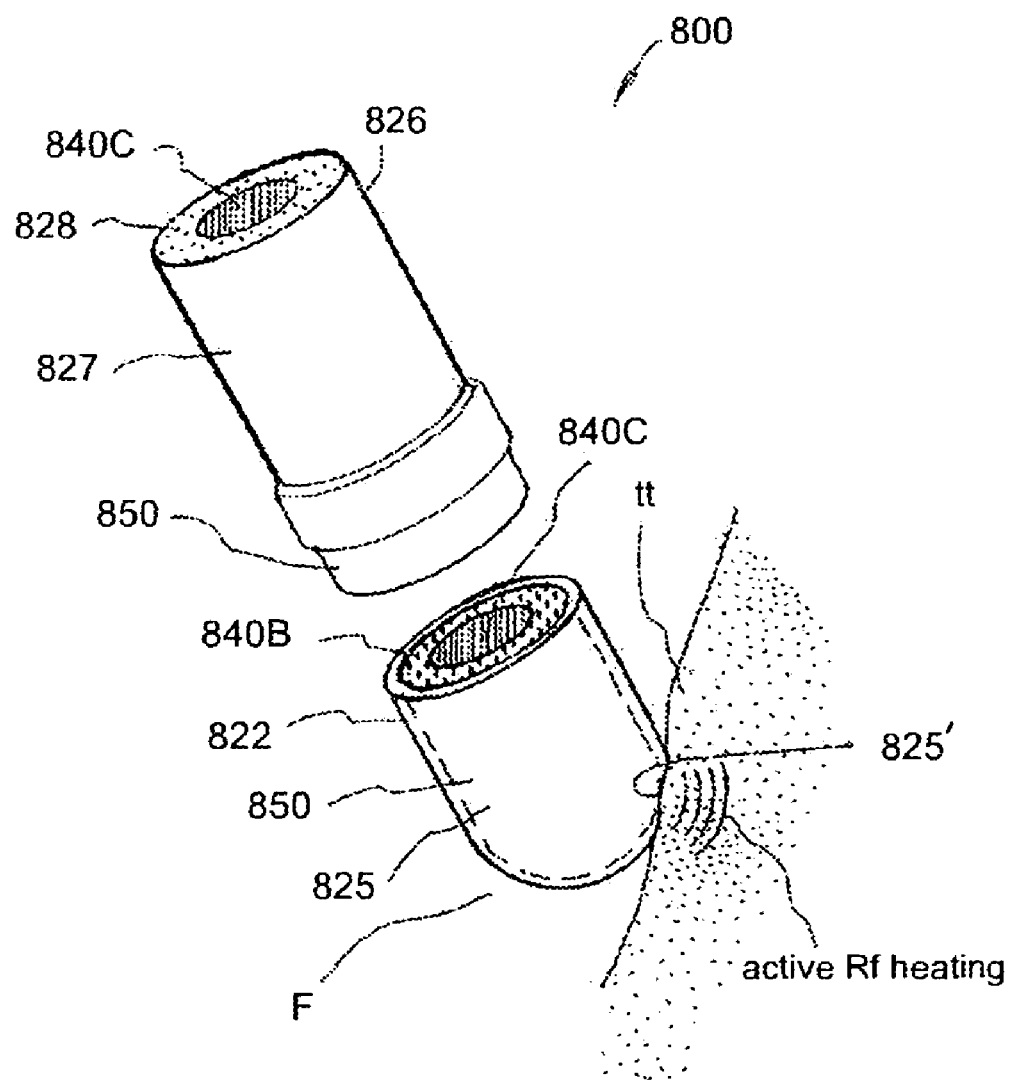
FIG. 27 is a view of the working end of an alternative Type "G" probe corresponding to the invention that carries a pressure-sensitive resistive layer and further showing its method of use for shrinking collagen in joint capsule.

Another Type "G" probe 800 and its method of use in a fluid environment is shown in FIG. 27. The working end 822 is carried at the distal end of a rigid probe body that can be used in an arthroscopic procedure. In one example, the targeted tissue tt is the surface of a patient's joint capsule that is "painted" with the engagement plane 825 of the working end 822. Such a procedure can be used to shrink collagen in the joint capsule to tighten the joint, such as in a patient's shoulder.

FIG. 27 illustrates that probe 800 has a body portion 826 that is proximal to the engagement plane or surface 825. In one embodiment, the exterior surface 827 of body portion 826 is an insulative material indicated at 828. An interior body portion of the working end 822 is of a variably resistive matrix 840B as described previously. A conductive body portion 840C (or electrode) at the interior of the probe is connected to a voltage source as described previously. The matrix 840B can be a PTC or NTC material, and in one embodiment is a rigid ceramic-type PTC material that is temperature sensitive. Of particular interest, an exterior layer 850 of a pressure-sensitive resistor is carried about the working end in contact with the variably resistive matrix 840B. The variably resistive layer 850 can be substantially thin and fabricated as previously described, for example, using Product No. CMI 118-44 available from Creative Materials Inc., 141 Middlesex Rd, Tyngsboro, Mass. 01879. In the illustration of the probe's method of use in FIG. 27, it can be understood that any pressure against the pressure-sensitive resistive layer 850 will locally decrease its resistance to current flow therethrough. Thus, as the engagement plane 825 is painted across tissue the joint capsule with a fluid F in the workspace, Rf current will only flow through the localized engagement plane portion indicated at 825' where the pressure-sensitive resistive layer 850 is under pressure which lowers its resistance substantially to thereby allow current flow therethrough. The illustration of FIG. 27 assumes the probe causes highly localized active Rf heating in the tissue while operating in a mono-polar manner in cooperation with a ground pad (not shown). In operation, the probe working end will thus apply energy to tissue only at the point of contact and pressure with the engagement plane. The fluid F and collateral tissue regions will not be subject to ohmic heating. It should be appreciated that the probe also can operate in a bi-polar manner wherein the probe working end carried an opposing polarity electrode, e.g., about the exterior surface 827 of the probe (see FIG. 27). In this embodiment, the variably-resistive matrix 840]B can modulate current flow exactly as described in previous embodiments to maintain the tissue temperature in contact with the engagement plane portion 825' at, or within, a selected temperature range.

It should be appreciated that the scope of the apparatus and method of the includes the use of a probe that does not carry a body portion of a variably-resistive matrix. In other words, the working end can rely only on the pressure-sensitive resistive layer 850 about the engagement plane 825 to locally apply energy to engaged tissues (see FIG. 27).

In another embodiment (not shown), the working end of the probe can have an elongate core of the substantially resistive material, e.g., either in a rod-like member or in a helical member. This resistive material has a fixed resistivity and is adapted to pre-heat the working end and the engaged tissue as a means of preconditioning certain tissues to have a certain impedance. Such a probe may be useful when the engagement surface is large. A thermally conductive, but electrically insulative, layer is disposed intermediate the core resistive material and a conductive (electrode) layer. The conductive layer is coupled in series with the resistive material to the remote voltage source. The variably resistive matrix is disposed between the engagement plane and the conductive (electrode) layer—as described in any of the Types "A" to "G" embodiments.

Figure 28:
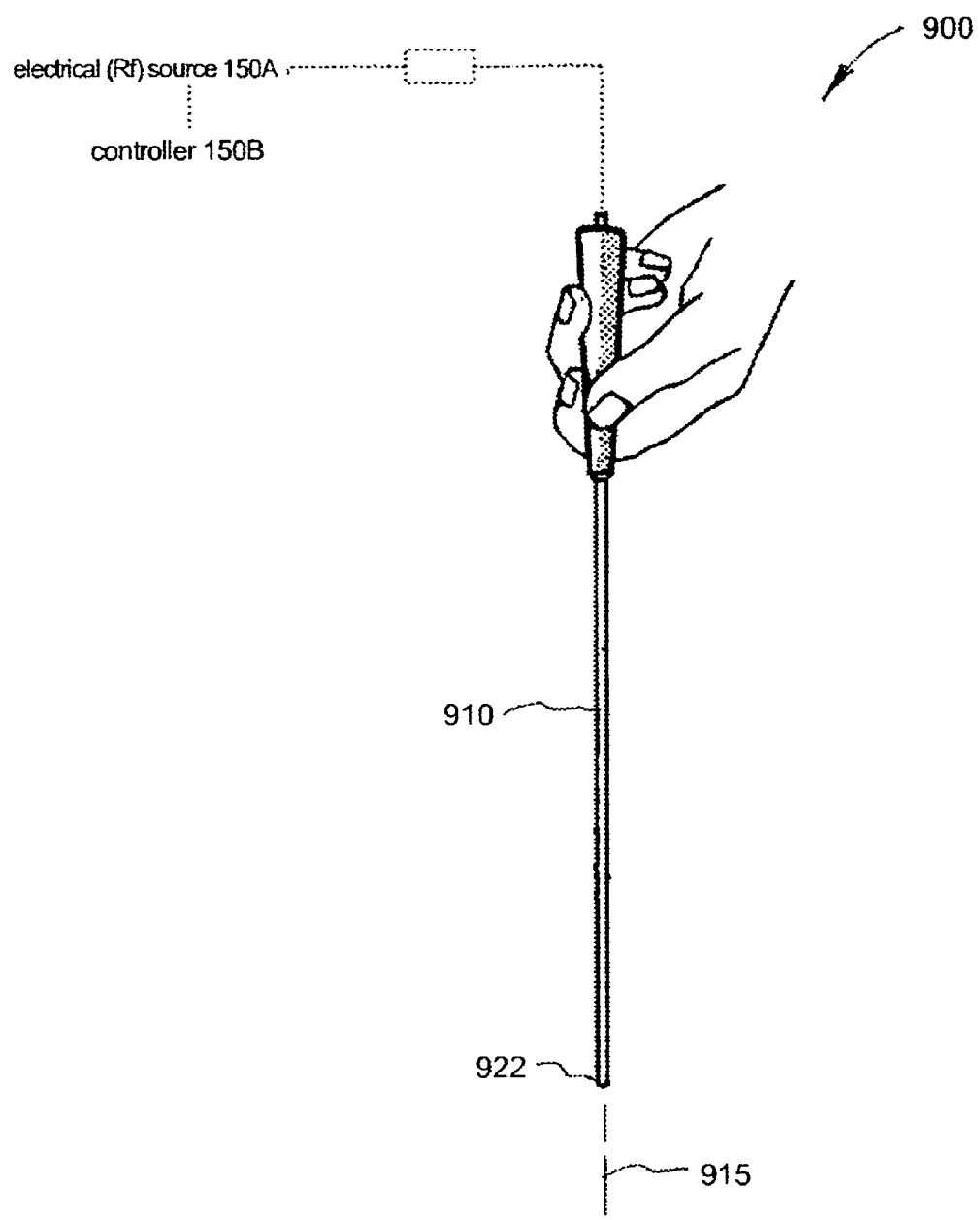
FIG. 28 is a plan view of a Type "H" probe corresponding to the invention that carries a temperature-responsive engagement surface.
Figures 29, 30:
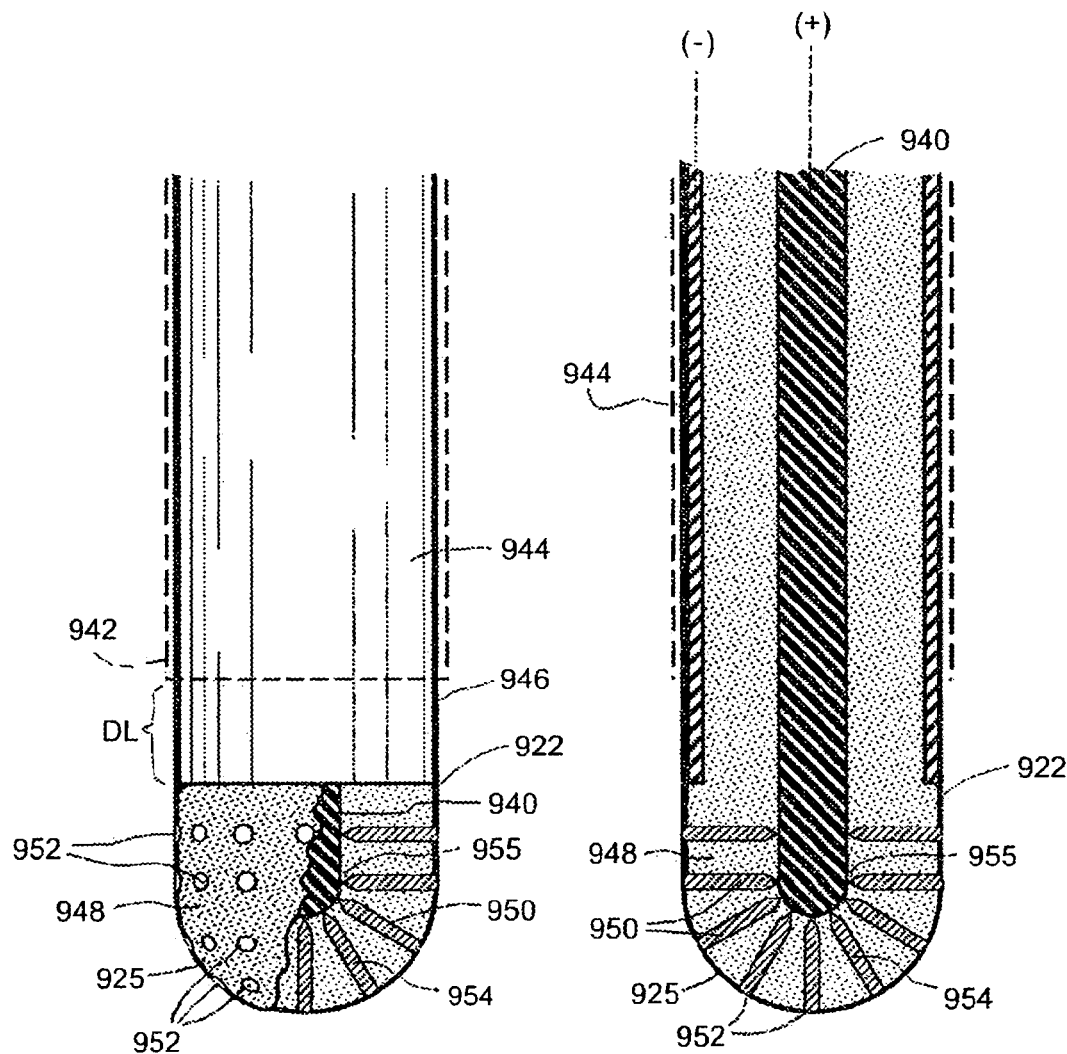
FIG. 29 is a cut-away view of the working end of the Type "H" probe of FIG. 28.
FIG. 30 is a full sectional view of the working end of FIG. 28.

7. Type "H" probe for energy delivery to tissue. FIGS. 28–30 illustrate a Type "H" probe 900 in accordance with the invention with a shaft portion 910 extending along axis 915. The probe's working end 922, and more specifically its engagement plane 925, is adapted for automatically modulating Rf energy delivery to engaged body structure in response to the temperature of the tissue and the working surface. A first described embodiment does not utilize the resistive matrix that was described in previous embodiments, but still relies on working surface materials that have different thermal expansion properties to provide self-modulating energy delivery to engaged tissue. In FIG. 29, it can be seen that the probe 900 has a rounded tip, for example as is used for electrosurgical energy delivery in arthroscopic procedures or other procedures for introduction into a lumen, space, or cavity in the patient's body. It should be appreciated that the invention of the working surface can be extended to sharp-tipped penetrating instruments, jaw surfaces and the like.

Referring to FIGS. 29 and 30, the working end defines an engagement plane 925 that extends around the circumference and rounded tip of the probe. The embodiment of FIG. 29 has a central core electrode 940 that can be any rigid or flexible conductive material that is coupled to electrical source 150A and optional controller 150B (FIG. 28). The outer sleeve 944 is of a conductive material such as a thin-wall metal hypotube that can serve as a return electrode in a bi-polar operating mode, although the core electrode 940 also can operate with a ground pad (not shown). In the bi-polar operating mode, the outer sleeve 944 has and exposed outer surface 946, or at least a distal length DL of the outer surface 946 is exposed to serve as an electrode. An optional outer insulator 947 is shown in phantom view, and this insulator layer 947 also may be axially translatable in the direction of the arrow in FIG. 29 to provide different exposed electrode surface areas to control depth of ohmic tissue heating.

A surface layer 948 of an insulator material is disposed at the end of the probe surrounding the core electrode 940 wherein the exposed exterior of the surface layer 948 defines the engagement plane 925. The surface layer 948 preferably is of a somewhat flexible and resilient polymer, and in one preferred embodiment is a silicone or polyethylene. The scope of the invention encompasses any polymeric insulator material that has a thermal coefficient of expansion greater than that of the adaptive conductive elements or electrodes indicated at 950, for reasons that will be described below. The insulator can also comprise a ceramic in substantially thin surface layers 948.

Figures 31A, 31B:
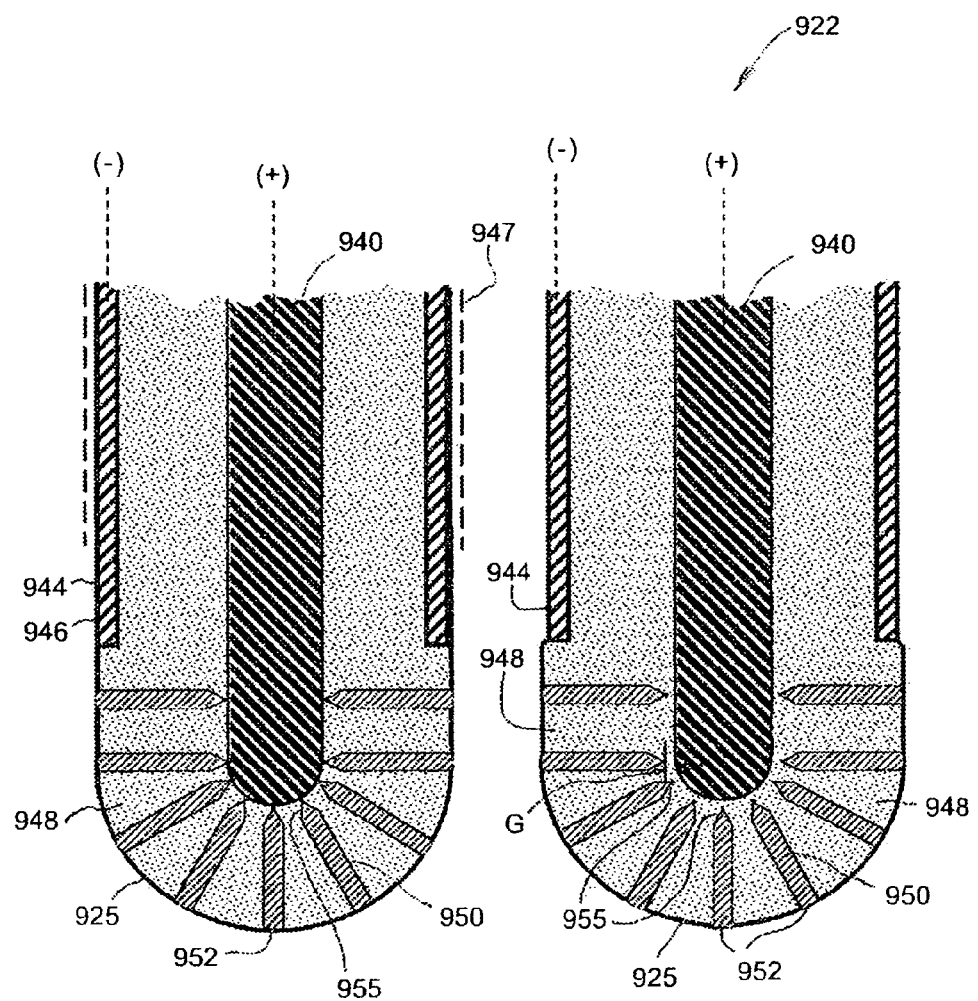
FIG. 31A is an enlarged sectional view of the working end of FIG. 28 with a resilient surface layer in a first position wherein Rf energy is delivered to engaged tissue.
FIG. 31B is a sectional view of the working end of FIG. 31A with the resilient surface layer in a second position wherein Rf energy is not delivered to engaged tissue.

Turning now to FIGS. 29–30, the cut-away views of the intermediate insulative working surface layer 948 show its thickness LT with the "adaptive" conductive elements or electrodes 950 extending therethrough. The electrodes are termed "adaptive" herein since the elements adapt from being an electrode to not being an electrode depending on the thermal expansion of the surface layer 948 in which the elements are embedded. As can be seen in FIG. 29, each conductive element 950 has a first end 952 with an exposed surface in the engagement plane 925, and a shaft portion 954 that extends to an inner tip (second end) 955 that contacts the core electrode 940 when the insulative surface layer 948 is in a first non-expanded low temperature position that extends over a selected temperature range. Referring now to FIG. 31A, in this first position of the insulator, the inner tip 955 of the element 950 couples it with the core electrode 940 to make the element an active electrode at its surface 952 in the engagement plane 925. FIG. 31B illustrates the insulative surface layer 948 in a second expanded higher temperature position that occurs at a selected treatment temperature, for example between 60 and 90° C. At this temperature range, the thermal expansion of the surface layer 948 exceeds that of the conductive element 950 so that the inner tips (second ends) 955 are de-coupled from the core electrode 940 to create a gap G, which will terminate active energy delivery at the exposed surface 952 of the element 950. It can be understood that active energy delivery will then be self-modulated by the temperature, and expansion-contraction, of the surface layer 948 and gap G at a temperature which defines a selected switching temperature or switching temperature range. The cooperation of the surface layer 948 and the conductive element 950 thus function as a type of localized switch to positively turn on and turn off the active energy delivery to engaged tissue. Of particular interest, the system functions to control active energy delivery to tissue in a highly localized manner—and the scope of the invention includes conductive elements 950 that have any very small cross-sectional dimensions in a working surface, any thickness of working surface layer, and any density of conductive elements 950 in a selected area of an engagement surface 925.

Figure 32:
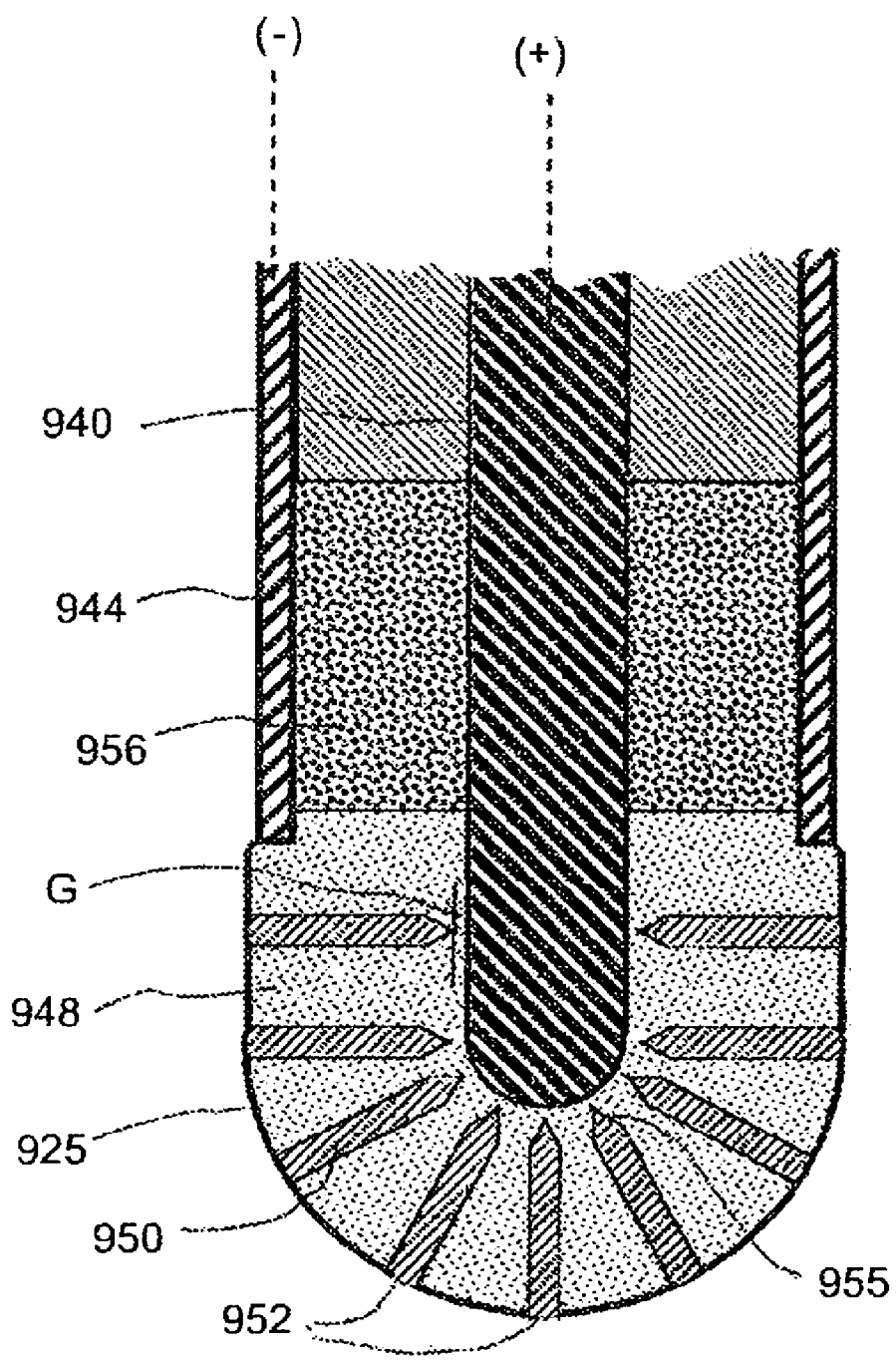
FIG. 32 is a sectional view of an alternative working end that carries a resistor component proximal to the engagement surface.

In another preferred embodiment shown in FIG. 32, the surface layer 948 is anon-conductive material or elastomer that functions as illustrated in the embodiment of FIGS. 29, 30, 31A and 31B. In FIG. 32, an additional component is added to the invention which comprises a resistive element 956 having substantially high resistance that extends between the core conductor 940 and the return electrode sleeve 944. The resistive element 956 is positioned anywhere in the probe 900 or the system that is intermediate the electrical source 150A and the surface layer 948 that carries the engagement plane 925. In one embodiment, as shown in FIG. 32, the resistor element 956 is carries in the probe just proximal to the engagement surface 925. Of particular interest, the resistor component 956 can enhance the principal mode of operation of the working end wherein the second ends 955 of elements 950 is cycled in and out of conductive contact with core conductor 940 as the surface layer 948 expands and contracts due thermal effects therein. In switch-like movements of the second ends 955 of elements 950, at an instant in time there will be a tendency to cause an arc of electrical energy across the gap G as it widens. As the resistance across the gap G increases to a selected level, the selected resistance of the resistor component 956 will be exceeded so that energy will slightly flow through the resistor component 956 from the core conductor 940 to the return electrode 944. By selecting a particular resistance, depending on the electrosurgical procedure, this type of shunting of current flow can prevent an arc across the resistive gap G that is created during the operation of the probe. Without such a resistor component 956, it can be understood that long durations of cycling the second ends 955 of the conductive elements 950 relative to the core conductor 940 would cause electrical arcs to degrade contact surfaces between the conductive elements 950 and core conductor 940. The use of resistor component 956 of the invention would eliminate such electrical arcing.

In another working end 922 that is similar to that of FIGS. 29, 30, 31A and 31B, the surface layer 948 itself can be a conductive-resistive matrix of the type in Types "A"–"G" that defines of temperature coefficient of resistance, or more particularly a positive temperature coefficient of resistance. This type of working end also would assist in preventing electrical arcs across any expanding gaps G between the second ends 955 of elements 950 and the core conductor 940 as the surface layer 948 expands and contracts.

Figure 33:
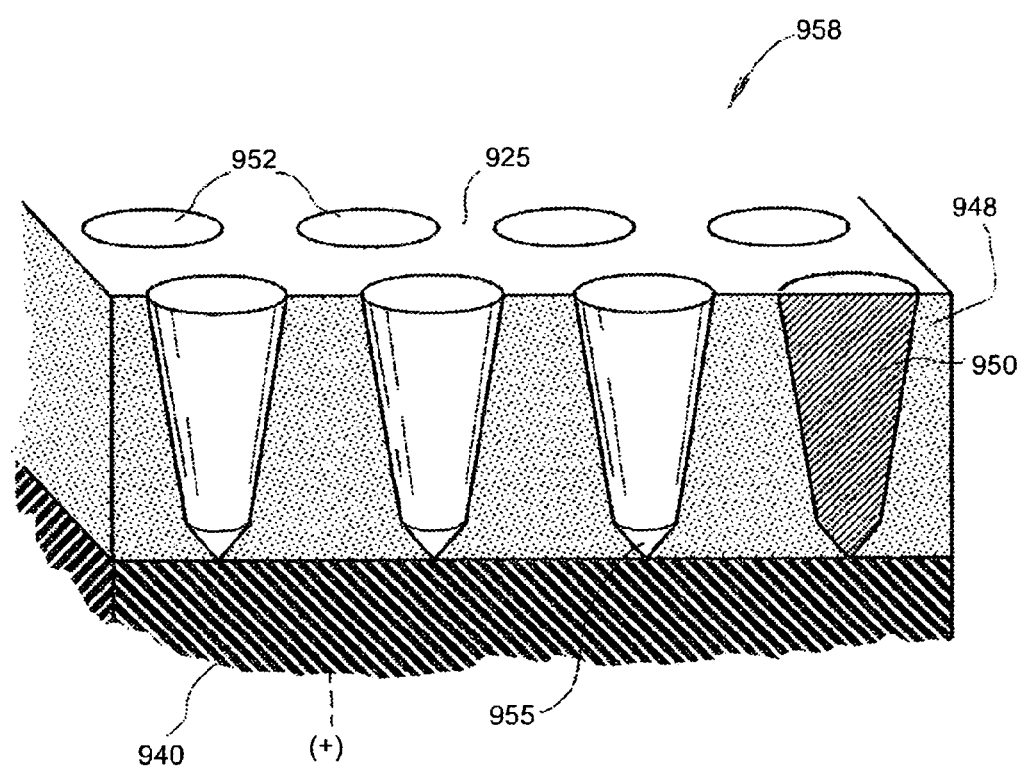
FIG. 33 is a sectional view of a portion of an alternative working end and engagement surface in a jaw face that is otherwise similar to FIGS. 29–30.

FIG. 33 illustrates the working surface 925 of the invention that is extended to a face of jaw member 958, which can be a surface of opposing jaws that open and close as in the embodiment shown in FIG. 22. The interior core conductive portion 940 again is covered with a surface layer 948 of an insulative material as first described above. The surface layer 948 also can be a resistive matrix for preventing electrical arcing between the conductive elements and the core electrode. The first end 952 of the conductive element 950 is exposed in the engagement surface 925 with the second end tip 955 adapted to physically couple with the core electrode 940 depending on the temperature of the surface layer 948. As can be seen in FIG. 33, the conductive element 950 can be tapered or have any other shape or cross-section and fall with in the scope of the invention. The conductive element 950 also can have surface asperities or any other feature such an annular grooves to insure that the element remains locked and embedded in the surface layer 948. In all other respects, the engagement surface would operate as described previously to modulate energy delivery to tissue in response to localized engagement pressure.

Figure 34:
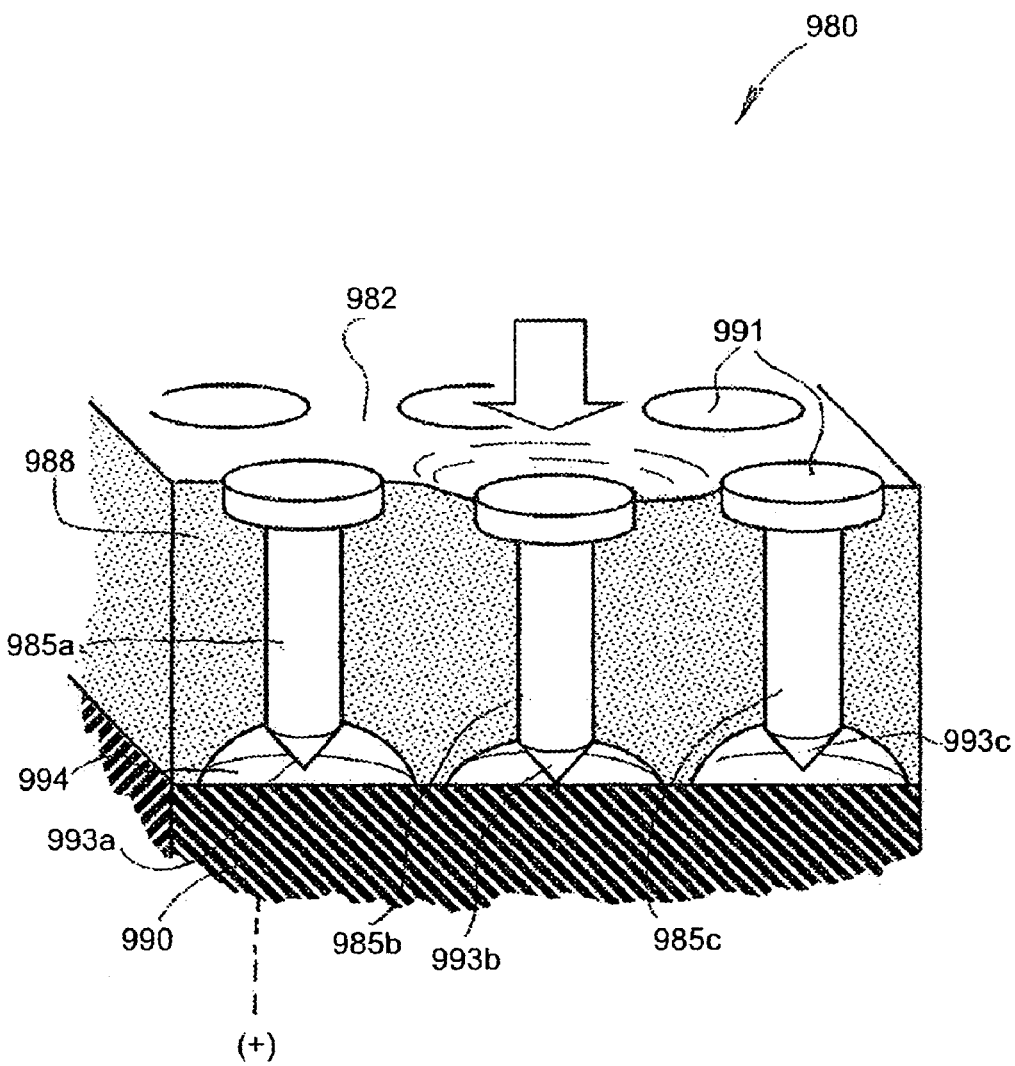
FIG. 34 is a sectional view of an alternative working end and engagement surface that locally delivers Rf energy in response to engagement pressure.
Figure 35:
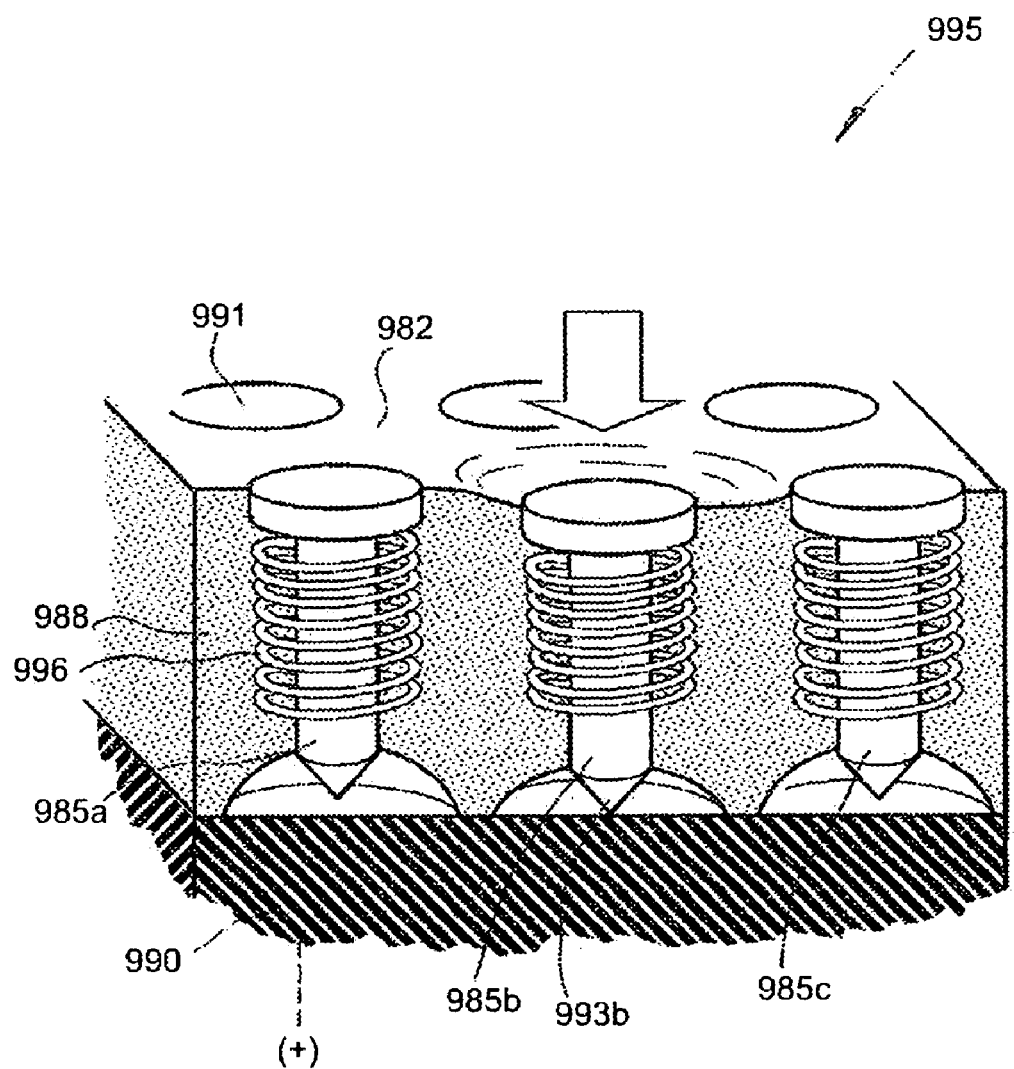
FIG. 35 is a sectional view of another alternative engagement surface that locally delivers Rf energy in response to pressure.

FIGS. 34 and 35 illustrate an alternative working end 980 of a probe or jaw face in accordance with the invention. The working end 980 operates on different principals than the embodiments of FIGS. 29–33, but with a similar assembly and fabrication approach. The embodiment of FIG. 34 shows a flat engagement plane 982 of a jaw face but such a plane also can be the circumference, or rounded surface, of any probe. The probe's engagement plane 982 again is adapted for modulating Rf energy delivery to the engaged body structure without the use of thermocouples and feedback circuitry. In this version, the probe utilizes contact "pressure" to actuate a plurality of highly localized switch-like elements 985a–985c to locally deliver Rf energy to engaged tissue. As can be seen in FIG. 34, a resilient surface layer 988 is provided over an interior conductive portion 990 that is coupled to an electrical source. The first ends 991 of conductive switch elements 985a–985c are exposed in the engagement plane 982. In a first position wherein the local engagement plane 982 does not engage tissue or only lightly engages tissue, the laterally outward switch elements 985a and 985c have second ends 993a and 993c that do not contact the interior conductive portion 990 so that Rf energy is not delivered to the engaged tissue. In FIG. 34, it can be seen further that the more central switch element 985b is within a region of the resilient surface layer 988 that is pressed with more force against the tissue and depressed (see arrow) such that the second end 993b of switch element 985b is pushed into contact with the interior conductive portion 990. By this means, Rf energy can be delivered only to those localized portions of tissue against which the engagement plane 982 is firmly pressed. In FIG. 34, the second ends 993a–993c of the switch elements 985a–985c are shown as being disposed in an open concavity 994 formed into the surface layer 988 adjacent the core electrode, but this is optional and the surface layer 988 can be any suitable layer, or multiple layers that have the required elasticity to perform the method of the invention described above. FIG. 35 illustrates an alternative embodiment of working end 995 that functions the same as the embodiment of FIG. 33, except with the addition of a helically coiled springs 996 embedded in the surface layer around the switch elements 985a–985c to control the pressure sensitivity of the engagement surface. It should be appreciated that such spring elements can be fashioned to operate within a substantially rigid surface layer with the switch elements 985a–985c spring-loaded in a bore to perform the method of the invention in creating pressure-controlled Rf energy delivery.

Those skilled in the art will appreciate that the exemplary systems, combinations and descriptions are merely illustrative of the invention as a whole, and that variations of components, dimensions, and compositions described above may be made within the spirit and scope of the invention. Specific characteristics and features of the invention and its method are described in relation to some figures and not in others, and this is for convenience only. While the principles of the invention have been made clear in the exemplary descriptions and combinations, it will be obvious to those skilled in the art that modifications may be utilized in the practice of the invention, and otherwise, which are particularly adapted to specific environments and operative requirements without departing from the principles of the invention. The appended claims are intended to cover and embrace any and all such modifications, with the limits only of the true purview, spirit and scope of the invention.

What is claimed is:

1. A method for controlled energy delivery to tissue, the method comprising:
   providing an electrosurgical probe having a working end comprising an internal conductor, an insulative layer and a conducive element extending through the insulative layer with one end of the element in electrical contact with the internal conductor and the other end exposed on the probe surface;
   engaging tissue at a tissue site with the working end;
   delivering Rf energy to the tissue site through the conductive element; and
   modulating the delivery of Rf energy to the tissue site by thermally altering a dimension of the insulative layer to move the conductive element out of or into electrical contact with the internal conductor.

2. The method of claim 1, wherein the probe is operated in an bipolar mode.

3. The method of claim 1, wherein the working end has a curved or semicircular shape.

4. The method of claim 1, wherein the conductive element is in electrical contact with the internal conductor at a first temperature and out of electrical contact at a second higher temperature.

5. The method of claim 1, wherein the insulative layer thermally expands to move the element out of electrical contact with the internal conductor.

6. The method of claim 5, wherein the thermal expansion of the insulative layer occurs at a temperature in the range of about 60 to 90° C.

7. The method of claim 1, wherein the insulative layer thermally contracts to move the element into electrical contact with the internal conductor.

8. The method of claim 1, wherein the dimension is a thickness.

9. The method of claim 1, wherein the conductive element includes a plurality of conductive elements.

10. The method of claim 9, wherein the conductive elements are distributed along a perimeter of the probe surface.

11. The method of claim 9, further comprising:
    utilizing the plurality of conductive elements to modulate the deliver of energy to the tissue site in a highly localized manner.

12. The method of claim 9, further comprising:
    delivering energy to the tissue site where a first portion of the plurality of conductive elements are electrically coupled to the internal conductor and a second portion are electrically decoupled from the internal conductor.

13. The method of claim 1, wherein the tissue site includes a tumor, cardiac tissue, or a collagen structure.

14. The method of claim 1, wherein the insulative element layer comprises an elastomer.

15. The method of claim 1, wherein delivery of energy to the tissue site is modulated responsive to a temperature of the insulative layer.

16. The method of claim 1, further comprising:
    utilizing the conductive element and the insulative layer as a localized switch to modulate the delivery of energy to the tissue site.

17. The method of claim 1, further comprising:
    creating a gap between an end of the conductive element and the inner conductor.

18. The method of claim 17, further comprising:
    utilizing the gap to switch the delivery of energy to the tissue site off and on.

19. A method for controlled energy delivery to tissue, the method comprising:
    providing an electrosurgical probe having a working end comprising an internal conductor, an insulative layer and a conductive element extending through the insulative layer with one end of the element in electrical contact with the internal conductor and the other end exposed on the probe surface;
    engaging tissue at a tissue site with the working end;
    delivering Rf energy to the tissue site through the conductive element; and
    modulating the delivery of Rf energy to the tissue site by thermally expanding and contracting the insulative layer to move the conductive element out of or into electrical contact with the internal conductor.

* * * * *

UNITED STATES PATENT AND TRADEMARK OFFICE
CERTIFICATE OF CORRECTION

PATENT NO. : 7,125,409 B2 Page 1 of 1
APPLICATION NO. : 11/315418
DATED : October 24, 2006
INVENTOR(S) : Csaba Truckai et al.

It is certified that error appears in the above-identified patent and that said Letters Patent is hereby corrected as shown below:

Claim 2, column 25, lines 52-53, delete the phrase "...wherein the probe is operated in an bipolar mode." and insert the correct phrase --...wherein the probe is operated in a bipolar mode.--.

Claim 11, column 26, line 19, delete the phrase "...the deliver of energy to..." and insert the correct phrase --...the delivery of energy to...--.

Signed and Sealed this

Sixth Day of March, 2007

JON W. DUDAS
*Director of the United States Patent and Trademark Office*

UNITED STATES PATENT AND TRADEMARK OFFICE
CERTIFICATE OF CORRECTION

PATENT NO.        : 7,125,409 B2
APPLICATION NO.   : 11/315418
DATED             : October 24, 2006
INVENTOR(S)       : Csaba Truckai and John Shadduck Page 1 of 1

It is certified that error appears in the above-identified patent and that said Letters Patent is hereby corrected as shown below:

Claim 1, Column 25, Line 41: Replace the word "conducive" with the word "conductive".

Signed and Sealed this
Twelfth Day of July, 2011

David J. Kappos
*Director of the United States Patent and Trademark Office*